US009155761B2

(12) United States Patent
McKenna et al.

(10) Patent No.: US 9,155,761 B2
(45) Date of Patent: Oct. 13, 2015

(54) METHOD FOR THE TREATMENT OF CANCER

(71) Applicant: UNIVERSITY COLLEGE CORK, NATIONAL UNIVERSITY OF IRELAND, CORK, Co. Cork (IE)

(72) Inventors: Sharon McKenna, Co. Cork (IE); Gerald C. O'Sullivan, Cork (IE); Tracey O'Donovan, Co. Cork (IE)

(73) Assignee: University of College Cork, National University of Ireland, Co. Cork (IE)

( * ) Notice: Subject to any disclaimer, the term of this patent is extended or adjusted under 35 U.S.C. 154(b) by 0 days.

(21) Appl. No.: 13/784,903

(22) Filed: Mar. 5, 2013

(65) Prior Publication Data
US 2014/0120182 A1    May 1, 2014

Related U.S. Application Data

(62) Division of application No. 12/836,626, filed on Jul. 15, 2010, now Pat. No. 8,431,587.

(60) Provisional application No. 61/225,949, filed on Jul. 16, 2009.

(51) Int. Cl.
| A61K 33/24 | (2006.01) |
| A61K 31/282 | (2006.01) |
| A61K 33/14 | (2006.01) |
| A61K 31/436 | (2006.01) |
| A61K 31/513 | (2006.01) |
| A61K 45/06 | (2006.01) |

(52) U.S. Cl.
CPC .............. A61K 33/14 (2013.01); A61K 31/282 (2013.01); A61K 31/436 (2013.01); A61K 31/513 (2013.01); A61K 33/24 (2013.01); A61K 45/06 (2013.01)

(58) Field of Classification Search
None
See application file for complete search history.

(56) References Cited

U.S. PATENT DOCUMENTS

2011/0293746 A1    12/2011  Yu

OTHER PUBLICATIONS

Aissat et al., Antiproliferative effects of rapamycin as a single agent and in combination with carboplatin and paclitaxel in head and neck cancer cell lines, Cancer Chemotherapy and Pharmacology, Jul. 2008, vol. 62, Issue 2, pp. 305-313.*
Tasdemir et al., Regulation of autophagy by cytoplasmic p53, Nature Cell Biology 10, 676-687 (2008), published online: May 4, 2008.*
Amaravadi and Thompson, Clin Cancer Res, 13(24):7271-7279 (2007). "The roles of therapy-induced autophagy and necrosis in cancer treatment".
Berry and Baehrecke, Cell, 131:1137-1148 (2007). "Growth arrest and autophagy are required for salivary gland cell degradation in *Drosophila*."
Clarke, Anat Embryol, 181:195-213 (1990). "Developmental cell death: morphological diversity and multiple mechanisms."
Debnath et al., Autophagy, 1(2):66-74 (2005). "Does autophagy contribute to cell death?"
Degenhardt et al., Cancer Cell, 10:51-64 (2006). "Autophagy promotes tumor cell survival and restricts necrosis, inflammation, and tumorigenesis."
Degterev and Yuan, Nature, 9:378-390 (2008). "Expansion and evolution of cell death programmes."
Jin and White, Autophagy, 4(5):563-566 (2008). "Tumor suppression by autophagy through the management of metabolic stress."
Kanzawa et al., J Neurosurg, 99:1047-1052 (2003). "Inhibition of DNA repair for sensitizing resistant glioma cells to temozolomide."
Kanzawa et al., Cell Death and Differentiation, 11:448-457 (2004). "Role of autophagy in temozolomide-induced cytotoxicity for malignant glioma cells."
Lam et al., Molecular Biology of the Cell, 19:691-700 (2008). "The inositol 1,4,5-trisphosphate receptor is required to signal autophagic cell death."
Mizushima, Genes Dev, 21:2861-2873 (2007). "Autophagy: process and function."
Mizushima et al., Nature, 451:1069-1075 (2008). "Autophagy fights disease through cellular self-digestion."
Opipari, Jr. et al., Cancer Research, 64:696-703 (2004). "Resveratrol-induced autophagocytosis in ovarian cancer cells."
O'Sullivan et al., Gastroenterology, 116:543-548 (1999). "Micrometastases in esophagogastric cancer: high detection rate in resected rib segments."
Pattingre et al., Cell, 122:927-939 (2005). "Bcl-2 antiapoptotic proteins inhibit Beclin 1-dependent autophagy."
Raguz and Yague, British Journal of Cancer, 99:387-391 (2008). "Resistance to chemotherapy: new treatments and novel insights into an old problem."

(Continued)

*Primary Examiner* — Svetlana M Ivanova
(74) *Attorney, Agent, or Firm* — Nixon Peabody LLP; David S. Resnick; Candace Summerford

(57) ABSTRACT

The invention is based on the surprising finding that treatment with a chemotherapeutic agent such as 5-fluorouracil (5-FU) and an autophagy inducer effectively inhibit the continued growth of, and prevent the recovery following drug withdrawal, of cancer cells. In vivo, drug resistance from a failure to adequately engage in apoptotic programmed cell death leads to a recurrence of cancer and tumors can remain dormant for periods of time before re-emerging as drug resistant metastases. It has been hypothesized that autophagy (Type II cell death) may help cancer cells survive in response to growth limiting conditions, such as nutrient depletion, hypoxia, absence of growth factor, or presence of cytotoxic drug. LiCl is a known autophagy inducer and accelerates cell survival to autophagic programmed cell death.

5 Claims, 24 Drawing Sheets

(56) References Cited

OTHER PUBLICATIONS

Ricci and Zong, The Oncologist, 11:342-357 (2006). "Chemotherapeutic approaches for targeting cell death pathways."
Ryan et al., Journal of Surgical Research, 117:121-126 (2004). "Prevalence of bone marrow micrometastases in esophagogastric cancer patients with and without neoadjuvant chemoradiotherapy."
Sant et al., Annals of Oncology, 14(Supp.5):v61-v118 (2003). "EUROCARE-3: survival of cancer patients diagnosed 1990-94—results and commentary."
Scarlatti et al., Cell Death and Differentiation, 15:1318-1329 (2008). "Role of non-canonical Beclin 1-independent autophagy in cell death induced by resveratrol in human breast cancer cells."
Scarlatti et al., Cell Death and Differentiation, 16:12-20 (2009). "Does autophagy have a license to kill mammalian cells?"
Takeuchi et al., Cancer Res, 65:3336-3346 (2005). "Synergistic augmentation of rapamycin-induced autophagy in malignant glioma cells by phosphatidylinositol 3-kinase/protein kinase B inhibitors."
Yorimitsu and Klionsky, Cell Death Differ, 12(Supp.2):1542-1552 (2005). "Autophagy: molecular machinery for self-eating."
Yu et al., PNAS, 103(13):4952-4957 (2006). "Autophagic programmed cell death by selective catalase degradation."
Zips et al., In vivo, 19:1-8 (2005).
Sikora, Current Science, 81(5):549-554 (2001).
Schmutzler et al., European Journal of Endocrinology, 143:15-24 (2000).

* cited by examiner

A.

METHOD FOR THE TREATMENT OF CANCER

CROSS REFERENCE TO RELATED APPLICATIONS

The present application is a divisional application of U.S. patent application Ser. No. 12/836,626 filed on Jul. 15, 2010, which claims benefit under 35 U.S.C. §119(e) of U.S. Provisional Application No. 61/225,949 filed on Jul. 16, 2009, the contents of each of which are incorporated herein by reference in their entireties.

INTRODUCTION

The present invention relates a method for the treatment of cancer, especially esophagogastric cancer. The invention also relates to a pharmaceutical composition for the treatment of cancer.

BACKGROUND TO THE INVENTION

Cancers of the esophagogastric region are highly malignant tumours with five-year survival rates of less than sixteen percent (Sant et al., 2003). Research has shown that 88% of patients, selected for curative resection for esophagogastric cancer, already have disseminated tumour cells (O'Sullivan G et al., 1999), that can remain dormant for variable periods, before emerging as aggressive, drug resistant metastases (Ryan et al., 2004). Improved systemic therapeutic options are therefore required to effectively eliminate primary and recurrent esophageal cancer.

Chemotherapeutic regimes are designed to induce maximum cancer cell killing, by engaging a cell death program. Drug resistance due to a failure to adequately engage programmed cell death (PCD) leads to recurrence of cancer. This is a major limitation, as de-regulation of cell death programs often plays a role in the development of the cancer in the first place (Raguz and Yague, 2008). Previously, apoptosis (Type I cell death) was regarded as the central mediator of PCD in response to chemotherapeutic agents. However, other death programs exist in eukaryotic cells (Ricci and Zong, 2006, Degterev and Yuan, 2008). Type II cell death is characterised by the formation of vesicles in the cytoplasm, loss of the cytoplasmic material and pyknosis of nuclear material within an intact nuclear membrane (Clarke, 1990). Evidence suggests that this morphology is a consequence of excessive autophagy. Several studies have now reported autophagic cell death in cultured mammalian cells (Pattingre et al., 2005, Yu et al., 2006, Opipari et al., 2004, Scarlatti et al., 2008, Debnath et al., 2005). Furthermore, autophagic programmed cell death has now been demonstrated during development of *Drosophila* and *Dictyostelium discoideum* (Berry and Baehrecke, 2007, Lam et al., 2008).

Autophagy is a highly conserved survival response to growth limiting conditions, in which cellular components are sequestered, degraded and released for re-cycling by autophagosomes (Yorimitsu and Klionsky, 2005). It is genetically regulated by a family of Atg genes (Mizushima, 2007) which have homologues in humans (e.g. human ortholog of Atg6-Beclin1). The role of autophagy in cancer remains controversial. Constitutive autophagy may be a necessary homeostatic process which removes damaged organelles and re-cycles macromolecules thus protecting against cancer (Mizushima et al., 2008). However, when a cancer is established—autophagy may take on new roles—it may help cancer cells survive in response to growth limiting conditions such as nutrient depletion, hypoxia, absence of growth factor and presence of cytotoxic drug (Jin and White, 2008, Degenhardt et al., 2006, Amaravadi et al., 2007). The induction of excessive autophagy may also be the major cell death mechanism that takes over when apoptosis is unavailable (Scarlatti et al., 2009). Autophagic cell death has been reported to be induced in malignant gliomas, ovarian and breast carcinoma by the chemotherapeutic agents temozolomide and Tamoxifen (Kanzawa et al., 2003, Kanzawa et al., 2004, Takeuchi et al., 2005, Opipari et al., 2004).

It is an object of the invention to overcome at least one of the above-referenced problems.

STATEMENTS OF THE INVENTION

The invention is based on the surprising finding that treatment with a chemotrerapeutic agent such as 5-fluorouracil (5-FU) and an autophagy inducer effectively inhibit the continued growth of, and prevent the recovery following drug withdrawal, of cancer cells. In vivo, drug resistance from a failure to adequately engage in apoptotic programmed cell death leads to a recurrence of cancer and tumours can remain dormant for periods of time before re-emerging as drug resistant metastases. It has been hypothesised that autophagy (Type II cell death) may help cancer cells survive in response to growth limiting conditions, such as nutrient depletion, hypoxia, absence of growth factor, or presence of cytotoxic drug. LiCl is a known autophagy inducer and accelerates cell survival to autophagic programmed cell death. The Applicant has shown that the combination of an autophagy inducer and a chemotherapeutic agent prevented the recovery of apoptosis competent and apoptosis incompetent cancer cells. The Applicant has also shown in an in vivo cancer model that the combination of an autophagy inducer and chemotherapeutic agent stops tumour growth and in fact reduces tumour volume to such an extent that the tumour disappears and does not return following cessation of treatment.

Accordingly, the invention broadly relates to a method of treatment and/or prevention of cancer in an individual comprising a step of administering to the individual a therapeutically effective amount of at least one chemotherapeutic agent and at least one autophagy inducer.

Suitably, the invention relates to a method for the treatment and/or prevention of a chemo-resistant cancer in an individual comprising a step of administering to the individual a therapeutically effective amount of at least one chemotherapeutic agent and at least one autophagy inducer.

In a preferred embodiment, the invention provides a method of treating an epithelial cancer, typically selected from lung, breast, colorectal and esophagogastric cancer, especially esophageal cancer, comprising administering to an individual in need thereof a therapeutically effective amount of at least one chemotherapeutic agent and at least one autophagy inducer.

Suitably, the chemotherapeutic agent is selected from a pyrimidine analogue (for example 5-FU) and a DNA-binding heavy metal ion complex such as platinum, palladium, ruthenium or osmium complex. In one embodiment, at least two chemotherapeutic agents are employed, for example 5-FU and a DNA-binding heavy metal ion complex.

Thus, in one embodiment, the methods of the invention comprise administering at least one autophagy inducer with at least two chemotherapeutic agents, for example 5-FU and oxaliplatin as chemotherapeutic agents and LiCl or an alternative autophagy inducer (for example rapamycin or a rapamycin derivative such as everolimus).

The invention also relates to a method of preventing recovery of cancer cells upon withdrawal of a chemotherapeutic agent, the method comprising a step of treating the cancer cells with an autophagy inducer. The cells may be treated with the autophagy inducer at the same time as they are treated with the chemotherapeutic agent, and/or they may be treated after the chemotherapeutic treatment has been withdrawn.

The invention also provides a pharmaceutical composition comprising a therapeutically effective amount of a chemotherapeutic agent and a therapeutically effective amount of an autophagy inducer. Typically, the ratio of autophagy inducer to chemotherapeutic agent is from 50:1 to 1:1, suitably from 20:1 to 2:1 (mg/kg body weight).

In another embodiment, the invention relates to the use of a chemotherapeutic agent and an autophagy inducer in the manufacture of a medicament for the treatment and or prevention of cancer.

The invention also relates to a pharmaceutical kit comprising an amount of a chemotherapeutic agent and an amount of an autophagy inducer.

Suitably, the composition or kit comprises one or more chemotherapeutic agents selected from 5-FU, and DNA-binding heavy metal ion complex (such as for example platinum complexes). In one embodiment, the composition or kit comprises at least one autophagy inducer, for example a lithium salt, and at least two chemotherapeutic agents (for example a pyrimidine analogue such as 5-FU and a DNA-binding heavy metal ion complex such as cisplatin, carboplatin or oxaliplatin).

Preferably, the pharmaceutical composition comprises:
a lithium salt and 5-FU, optionally in combination with a further chemotherapeutic agent;
a lithium salt and a platinum complex selected from oxaliplatin, carboplatin, and oxaliplatin, optionally in combination with a further chemotherapeutic agent;
a BH3 mimetic and 5-FU, optionally in combination with a further chemotherapeutic agent;
a BH3 mimetic and a platinum complex selected from oxaliplatin, carboplatin, and oxaliplatin, optionally in combination with a further chemotherapeutic agent;
rapamycin and 5-FU, optionally in combination with a further chemotherapeutic agent;
rapamycin and a platinum complex selected from oxaliplatin, carboplatin, and oxaliplatin, optionally in combination with a further chemotherapeutic agent;
everolimus and 5-FU, optionally in combination with a further chemotherapeutic agent; or
everolimus and a platinum complex selected from oxaliplatin, carboplatin, and oxaliplatin, optionally in combination with a further chemotherapeutic agent.

In another embodiment, the invention relates of a method for preventing the recovery of cancer cells comprising the steps of treating the individual with a therapeutically effective amount of chemotherapeutic agent and a therapeutically effective amount of an autophagy inducer.

The invention also relates to a method of treating an individual with cancer and who is undergoing treatment with a chemotherapeutic agent, the method comprising the step of co-treating the individual with a therapeutically effective amount of autophagy inducer.

In another embodiment, the invention relates to a method for treating an individual with cancer, the method comprising the step of treating the individual with a therapeutically effective amount of an autophagy inducer.

DEFINITIONS

Typically, the cancer is selected from the group comprising: esophagogastric cancer; fibrosarcoma; myxosarcoma; liposarcoma; chondrosarcoma; osteogenic sarcoma; chordoma; angiosarcoma; endotheliosarcoma; lymphangiosarcoma; lymphangioendotheliosarcoma; synovioma; mesothelioma; Ewing's tumor; leiomyosarcoma; rhabdomyosarcoma; colon carcinoma; colorectal carcinoma; pancreatic cancer; breast cancer; ovarian cancer; prostate cancer; squamous cell carcinoma; basal cell carcinoma; adenocarcinoma; sweat gland carcinoma; sebaceous gland carcinoma; papillary carcinoma; papillary adenocarcinomas; cystadenocarcinoma; medullary carcinoma; bronchogenic carcinoma; renal cell carcinoma; hepatoma; bile duct carcinoma; choriocarcinoma; seminoma; embryonal carcinoma; Wilms' tumor; cervical cancer; uterine cancer; testicular tumor; lung carcinoma; small cell lung carcinoma; bladder carcinoma; epithelial carcinoma; glioma; astrocytoma; medulloblastoma; craniopharyngioma; ependymoma; pinealoma; hemangioblastoma; acoustic neuroma; oligodendroglioma; meningioma; melanoma; retinoblastoma; primary and metastatic tumors, and leukemias. Typically, treatment of the cancer entails reducing one or more of survival, proliferation and migration of, or invasion by, cancer cells.

In this specification, the term "chemo-resistant cancer" should be taken to mean cancer cells that exhibit autophagy following exposure to chemotherapeutic agents.

In this specification, the term "treatment" should be taken to mean a course of action/dosing regime that either inhibits, delays or prevents the progression of cancer, including cancer metastasis, or that inhibits, delays or prevents the recurrence of cancer, including cancer metastasis, or that prevents or hinders the onset or development of cancer in an individual.

In this specification, the term "prevention" should be taken to mean prevention of the recurrence of cancer, at a local or distant site, typically following the withdrawal of chemotherapeutic drugs in an individual diagnosed with cancer.

In this specification, the term "chemotherapeutic agent" should be taken to mean an agent that induces cancerous cells to commit to cell death. Suitable chemotherapeutic agents will be known to those skilled in the art. Such chemotherapeutic agents include but are not limited to; alkylating agents, anti-metabolites, plant alkyloids and terpenoids, topoisomerase inhibitors, anti-tumour antibiotics, DNA-binding heavy metal ion-based complexes including but not limited to the platinum-based complexes cisplatin, carboplatin and oxaliplatin, and histone deacetylase (HDAC) inhibitors including hydroxamate-type HDAC inhibitors (SAHA, Pabinostat, Belinostat) and benzamide-type HDAC inhibitors (the details of which will be well known to those skilled in the art. Examples of suitable chemotherapeutic anti-metabolites include, purine analogues not limited to azathoprine, mercaptopurine, tioguanine and fludarabine; pyrimidine analogues not limited to 5-fluorouracil (5-FU), floxuridine and cytosine arabinoside; antifolates not limited to methotrexate, trimethoprim, pyrimethamine and pemetrexed. Suitably, the chemotherapeutic agent is a DNA damaging agent (to include DNA-binding agent). Preferably, it is a pyrimidine analogue, examples of which are provided above. Ideally, it is 5-FU.

In this specification, the term "autophagy inducer" should be taken to mean an agent which induces cancer cells to commit to an autophagic process. Suitable inducers of autophagy will be well known to those skilled in the art. One example is a lithium compound, for example a lithium salt. Examples of lithium salts are lithium chloride (LiCl) or any other pharmaceutically acceptable salts thereof, including but not limited to; lithium carbonate, lithium citrate, lithium sulfate, lithium aspartate, lithium orotate. Another example of a class of compounds that induce autophagy are BH3 mimetics such as, for example, HA14-1 (Sigma Ireland). For a detailed review on how BH3 mimetics are proposed as a promising anticancer agent see (Zhang et al., 2007). Rapamycin (also known as sirolimus), and rapamycin analogues, for example everolimus, temsirolimus, are further examples of autophagy inducers, the details of which will be well known to those skilled in the art.

In the specification, the term "individual" should be taken to mean a human; however it should also include higher mammals for which the therapy of the invention is practicable.

In this specification, the term "therapeutically effective amount" should be taken to mean an amount of a chemotherapeutic agent and an autophagy inducer which result in partial or total inhibition in the progression of cancer and prevent or inhibits the recurrence of cancer following withdrawal from an anti-cancer regime. In a particular, a therapeutically effective amount of a chemotherapeutic agent should be taken to mean an amount that results in a clinically significant number of cancer cells being killed. A therapeutically effective amount of an autophagy inducer should be taken to mean an amount that results in a clinically significant number of chemoresistant cancer cells being killed by means of Type II cell death. An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the type of chemotherapeutic agent; species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances. As an example, the following doses may be employed:

Cisplatin: high dose=6.9 mg/kg; low dose=2 mg/kg
Oxaliplatin: high dose=6/15 mg/kg; low dose=1.5/5 mg/kg;
Lithium Chloride: high dose=14.5/17 mg/kg; low dose=4.5/10 mg/kg
Rapamycin: high dose=2 mg/kg; low dose=0.6 mg/kg
5-Fluorouracil: high dose=87 mg/kg; low dose=8/12 mg/kg In this specification, the term "administering" should be taken to include any form of delivery that is capable of delivering the chemotherapeutic agent and the autophagy inducer to cancer cells including local delivery, intravenous delivery, oral delivery, intramuscular delivery, intrathecal delivery, transdermal delivery, inhaled delivery and topical delivery. Methods for achieving these means of delivery will be well known to those skilled in the art of drug delivery. The term should also encompass co-administration of the two active compounds, or administration at separate times. For example, the actives may be administered on alternate days, or on the same day at different times, or on different days of the week.

In one preferred embodiment, the drugs are co-administered. One suitable way of achieving this is the provision of both drugs in a unit dose form, for example a pharmaceutical formulation comprising the two drugs in the form of a tablet or a capsule. In the unit dose, the drugs may be admixed, or they may be kept separate in different parts of the unit dose. For example, the unit dose may be a capsule having the drugs separated into different compartments of the capsule.

The chemotherapeutic agent and an autophagy inducer may form part of the same pharmaceutical composition or may comprise separate components for administration in a therapeutically effective amount at the same or different times and in any order or sequence.

In this specification, the term "pharmaceutical composition" should be taken to mean compositions comprising a therapeutically effective amount of a chemotherapeutic agent and an autophagy inducer, and a pharmaceutically acceptable carrier or diluent. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the chemotherapeutic agent and an autophagy inducer is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like.

The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to, ease pain at the, site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

BRIEF DESCRIPTION OF THE FIGURES

As shown in FIG. 23a combination treatment (Oxaliplatin & Lithium) had a significant effect on tumour volume, following systemic delivery when compared to both single agent treatments Oxaliplatin and Lithium (*p=0.013 and *p=0.004 respectively). This combination treatment also enhanced survival when compared to either agent alone.

DETAILED DESCRIPTION OF THE INVENTION

Methods

Cell Lines and Culture Conditions

Figure 1:
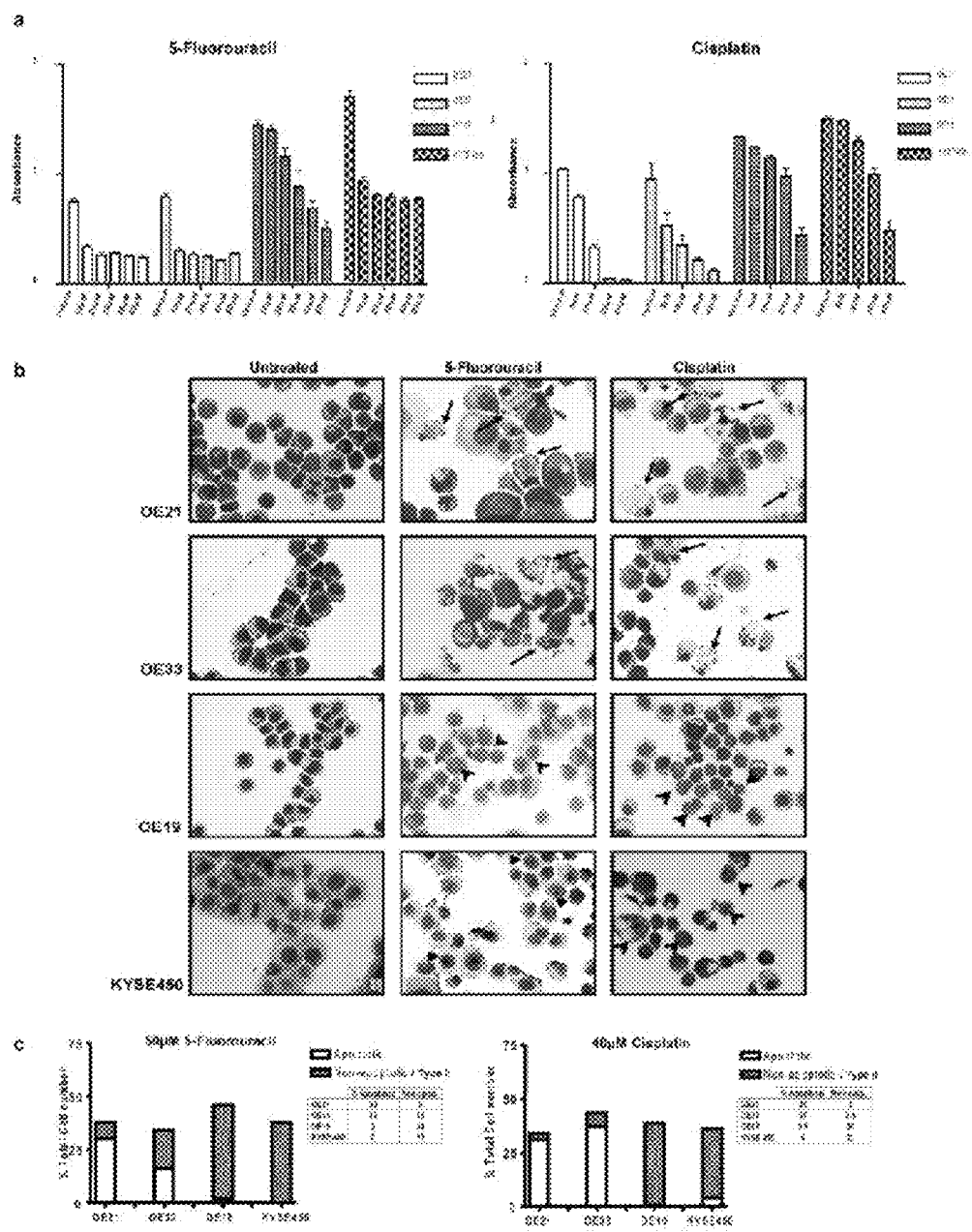
FIG. 1 Effect of 5-fluorouracil (5-FU) and cisplatin on viability and cell death morphology in esophageal cells. Cells were treated with a range of 5-FU (10-60 µM) and/or cisplatin (5-40 µM) concentrations for 48 hours. a MTT assay was used to determine the sensitivity of each cell line to 5-FU and cisplatin. Values represent the Mean absorbance+/−Standard Error of the Mean (S.E.M) (error bars) of four independent experiments. b Morphological features of all four esophageal cell lines (OE21, OE33, OE19 and KYSE450) treated with 5-FU (50 µM) and/or cisplatin (40 µM), for 48 hours. OE21 and OE33 treated cells display the morphological features of apoptosis (arrows), including cell shrinkage, chromatin condensation, DNA degradation and fragmentation into apoptotic bodies. Non-apoptotic cell death (arrowheads), evident in OE19 and KYSE450 cells, is characterized by pyknosis of the nuclear material and the development of cytoplasmic vesicles. c Demonstrates the extent of apoptotic (clear bars) and non-apoptotic (hatched bars) cell death in each cell line, in response to both 5-FU (50 µM) and cisplatin (40 µM) for 48 hours, determined by counting at least three fields of view per slide, with an average of 100 cells per field. Percentages were calculated and presented graphically.

Established human esophageal cell lines OE19, OE21 and OE33 were obtained from the European Collection of Cell Cultures. KYSE450 were from Die Deutsche Managementsystem Zertifizierungsgesellschaft mbH (DSMZ). All cell lines were maintained in RPMI 1640 medium, 1% penicillin/ streptomycin and 10% (v/v) foetal calf serum (Gibco, UK) and grown at 37° C., 5% $CO_2$.

Cell Growth/Viability

Cell growth/viability was assessed using the Real-Time Cell analyzer. Cells were seeded at $2.5\times10^4$ cells/cm$^2$, in a 96-well plate and treated for ~80 hours. To assess recovery, at 80 hours post treatment all drugs were removed, culture medium was replaced and cells were cultured for an additional 85 hours, to monitor their ability to recover. Viable cells remain adhered to the plate and the relative change in electrical impedance is measured to represent cell status. The cell index (CI) is a relative value, representing the impedance change divided by a background value. The greater the cell number adhered, the larger the impedance and as cells are lost, the impedance drops. Measurements are taken every fifteen minutes for the first three hours after seeding and treatment, all other measurements of impedance are taken continually, every hour.

Additionally, a change in a cell status, such as morphology, cell adhesion or cell viability can lead to a change in CI.

MTT Viability Assay

Viability of esophageal cells was assessed using the MTT reduction assay. Cells are seeded at $2\times10^4$ (OE33/OE19) and $1\times10^4$ (OE21/KYSE450) cells per cm², treated for 48-96 hours and incubated for an additional 60 minutes at 37° C. in 0.5 mg/ml MTT dye. Viable, metabolizing cells reduce MTT dye, producing a dark formazan product, with absorbance read at 562 nm, reference wavelength 620 nm. To assess recovery, at 48 hours post treatment, in replicate plates (identical seeding & treatment times), all drugs were removed, culture medium was replaced, and these cells were cultured for a further 48-96 hours, to monitor their ability to recover and MTT assay was repeated.

Statistical Analysis

In analysis of MTT data, values are presented as the Mean absorbance+/−Standard Error of the Mean (S.E.M) for four independent experiments. Statistical analysis was performed with paired Student's t-test. Values of $p<0.05$ were considered statistically significant. Asterisks indicate the level of significance.

Evaluation of Morphology

Morphological features of cells treated with 5-fluorouracil (5-FU)/cisplatin, without and with 3-MA, LY294002, Bafilomycin, Lithium chloride, rapamycin or HA14-I were examined by light microscopy. Morphologies of treated cells were examined 24 and 48 hours post treatment, treatment times are referred to in figure legends. Aliquots of vehicle control and drug treated cells were cytospun onto glass slides and stained with Rapi-Diff (Braidwood laboratories, UK). The extent of apoptotic and non-apoptotic cell death was determined by counting the cells in at least three fields of view per slide, with an average of ~100 cells per field. Apoptotic cell death is characterized by the presence of two or more of the following morphological features: cell shrinkage, chromatin condensation, DNA degradation and fragmentation into 'apoptotic bodies', within an intact plasma membrane. Autophagic cell death was identified by clear elevation of cytoplasmic vesicles, loss of cytoplasmic material, pyknosis of the nuclear material and an intact nuclear membrane. Cytospin images are representative of at least three independent experiments.

Evaluation of Caspase-3 Activity

To examine control and 5-Fluorouracil treated cells for evidence of caspase activity cells were processed by trypsinization, 48 hours after treatment. Following fixation in 4% paraformaldehyde, cells were washed in a permeabilisation buffer (0.1% Triton, 0.1% sodium azide, 10 mM HEPES, 4% FCS, 150 mM NaCl) and incubated with a primary rabbit polyclonal anti-active caspase-3 antibody (BD Biosciences UK) on ice for 1 hr. This was detected with an anti rabbit FITC conjugated secondary antibody, and samples were analyzed by FACScan at 530 nm (FL-1). Percentages indicate the proportion of cells with active caspase-3, detected as an increase in the number of FITC (FL-1) labelled cells. Similar results were observed in at least three independent experiments.

Detection of Mitochondrial Depolarization ($\Delta\Psi m$)

Mitochondrial membrane potential was determined using the JC-1 probe (Molecular Probes). In non-apoptotic cells, JC1 accumulates as aggregates in the mitochondria, which stain red (FL2; 590 nm). At the onset of apoptosis, a loss of mitochondrial membrane potential ($\Delta\Psi m$) releases the aggregated JC1, returning it to its monomeric form, which stains the cytosol green (FL1; 530 nm). Therefore, fluorescence of the JC-1 probe in the FL-2 channel decreases as mitochondrial membrane integrity is lost, while the fluorescence in FL-1 channel increases. Cells were incubated in JC1 (7.5 μg/ml) at 37° C. for 15 mins, and washed prior to analysis by flow cytometry (FACScan, Becton Dickinson). Percentages denote the proportion of cells with depolarised mitochondria following 48 hour incubation with 5-Fluorouracil and represent at least three independent experiments.

Electron Microscopy

Cells were seeded on semi-porous membranes and incubated in 5-Fluoruracil (5-FU) for 48 hours. Cells were then fixed in a 0.165 mM phosphate buffer (pH 7.4), containing 2.0% glutaraldehyde, at room temperature (RT) for 40 minutes. Cells were post-fixed in Osmium tetroxide ($OsO_4$) at RT for 60 minutes, dehydrated in ascending grades of ethanol solutions (50%, 70%, 95%, 100% and 100% dry), prior to embedding in Araldite resin. Samples were subjected to a graded infiltration process with araldite (epoxy resin) before being set and sectioned. Representative areas were chosen for ultra-thin sectioning and samples were examined by electron microscopy.

Western Blotting and Antibodies

Total cellular protein extracts were prepared by scraping the cells into modified RIPA buffer (50 mM Tris HCl (pH 7.4), 150 mM NaCl, 0.25% Sodium deoxycholate, 1% Igepal, protease inhibitors 1 mM EDTA, 1× Pefabloc, 1× protease inhibitor cocktail, 1 mM $Na_3VO_4$, 1 mM NaF). All protein samples were separated by SDS-PAGE (10/12%) and electrophoretically transferred onto nitrocellulose membrane. All primary antibodies were incubated overnight at 4° C.: anti-phospho mTOR (Ser 2448) and anti-p70$^{S6K}$ (Thr 389) (Cell Signaling Technologies, UK), anti-Beclin-1 (BD Biosciences, UK) and anti-LC3 (Medical & Biological Laboratories, Japan). The membranes were incubated with the relevant horseradish peroxidase conjugated secondary antibodies (DakoCytomation, Dublin) and detected by chemiluminescence (ECL Amersham, UK).

Vacuolar Redistribution of GFP-LC3

To visualize and quantify the formation of autophagic vesicles, the green fluorescent protein (GFP)-LC3 (pEGFP-LC3) expression vector, kindly supplied by Dr. T. Yoshimori (National Institute of Genetics, Japan) was used. Cells were transiently transfected with the Amaxa electroporation system according to the supplier's protocol. Twenty-four hours post transfection, cells were treated with 5-FU and/or Cisplatin, fixed in 4% paraformaldehyde in PBS and transferred onto slides using a non-fluorescent fixative for analysis by fluorescence microscopy. Alternatively, Western Blot analysis was used to assess the expression and processing of LC3. Upon stimulation of autophagy, LC3 is up-regulated and processed from soluble GFP-LC3I (45 kDa) to the autophagosome-associated form GFP-LC3II (43 kDa). The membrane sequestered, lipid-conjugated form of LC3-II remains with the autophagosome membrane after the vesicle has formed, and levels of both isoform are detected by Western Blot. Transfection efficiency was consistent for a given cell line, OE33 and KYSE450 cell lines (~60-70%) compared to OE19 and OE21 cell lines (~30%).

Visualization of Monodansylcadaverine (MDC)-Labelled Vacuoles

MDC is an autofluorescent weak base that accumulates in acidic lysosomal vacuoles, showing high selectivity for autophagosomes, due to the high level of unhydrolyzed membrane lipids from engulfed organelles, which enhance MDC fluorescence. Cells were incubated with 0.1 mM MDC in PBS at 37° C. for 10 minutes (Biederbick et al., 1995), washed and immediately analyzed by fluorescent microscopy.

Gene Silencing

Gene silencing with siRNA was used to inhibit mammalian Beclin1 (ortholog of Atg6). Cells were transfected with a pre-designed siRNA (20-50 nM) against Beclin1 (Dharmacon ON-TARGETplus SMARTpool Human BECN1, NM_003766) using the transfection reagent Lipofectamine 2000 (Invitrogen, Ireland). The transfection efficiency was greater than 60% (Transfection efficiency was assessed visually using fluorescently tagged RNA duplexes, Dharmacon) and the extent of Beclin1 silencing was determined by Western Blot analysis of protein levels.

Results

Cell Death Induced by 5-Fluorouracil (5-FU) and Cisplatin in Esophageal Cancer Cells A panel of four esophageal cell lines was evaluated, two squamous (OE21/KYSE450) and two adenocarcinoma (OE19/OE33), for their sensitivity to the chemotherapeutic drugs 5-FU and cisplatin. At a range of drug concentrations, OE21 and OE33 cell lines are significantly more sensitive than OE19 and KYSE450 cell lines. For example, 10 µM cisplatin induced significant effects on cell viability in both OE21/OE33, while the OE19/KYSE450 cell lines were only marginally affected (FIG. 1a).

The more drug sensitive esophageal cell lines (OE21/OE33) induced a predominantly apoptotic cell death morphology (Type I PCD), in response to both 5-FU and cisplatin (arrows, FIG. 1b), with low levels of non-apoptotic cell death morphology. At 40 µM cisplatin, OE21 cells display 31% apoptotic/3% non-apoptotic cell death (FIG. 1c). The more drug resistant OE19/KYSE450 cell lines display predominantly non-apoptotic morphology (arrowheads, FIG. 1b) with OE19 cells displaying only 0.5% apoptosis/38% non-apoptotic cell death (FIG. 1c). This non-apoptotic morphology includes pyknosis of the nuclear material and vacuolization of the cytoplasm, features resembling those described for autophagic/Type II cell death.

Figure 2:
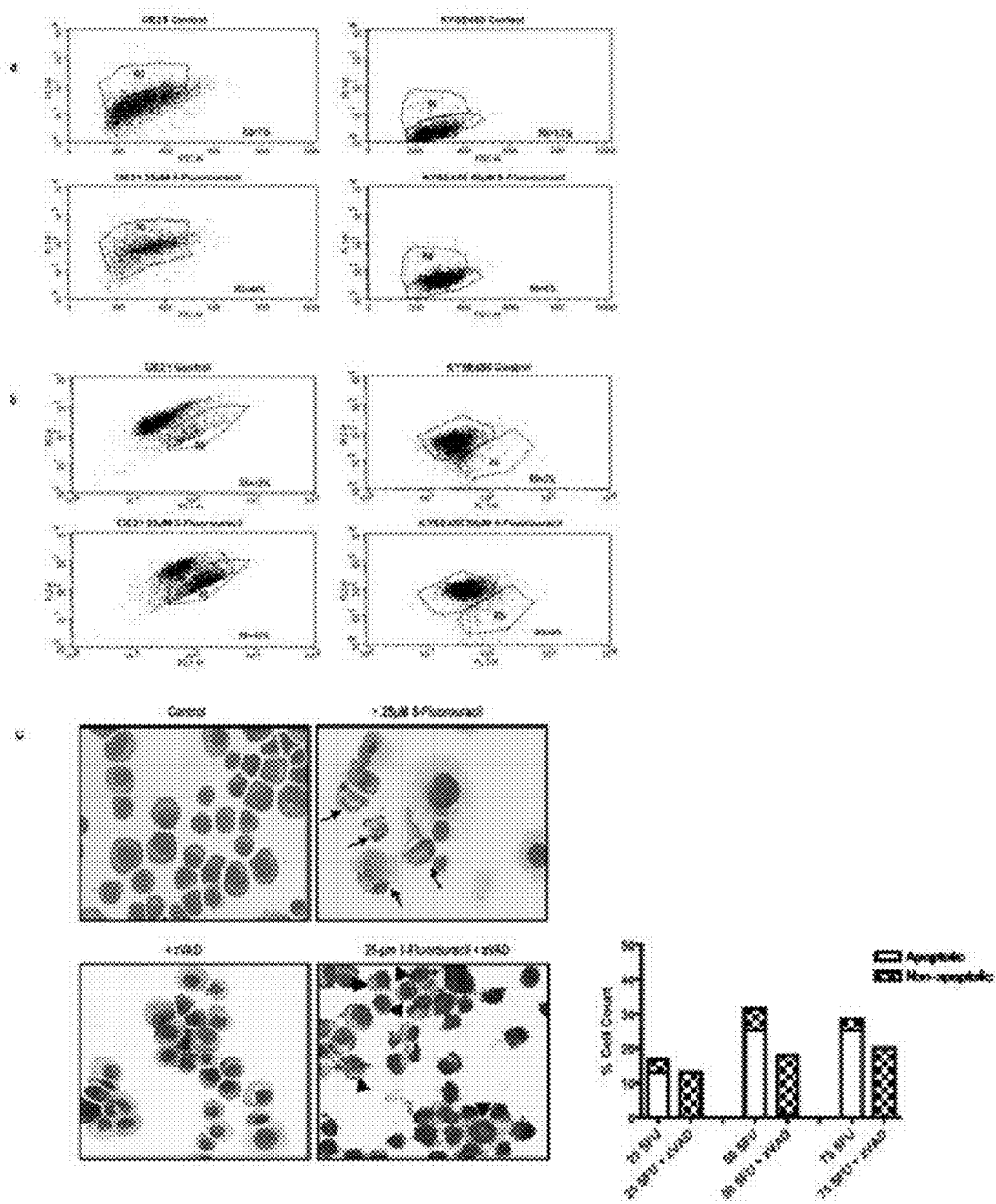
FIG. 2 Analysis of caspase activity and mitochondrial membrane potential. a Representative flow cytometric analysis of active caspase-3 in control and 5-fluorouracil (5-FU) (25 µM/50 µM) treated OE21 and KYSE450 cell lines. The percentages shown indicate the proportion of cells with active caspase-3, detected as an increase in the number of FITC (FL-1) labeled cells, with 44% of OE21 cells displaying active caspase-3 following drug treatment. More drug resistant, KYSE450 cells fail to show any active caspase-3 (range of concentrations tested). Results are representative of three independent experiments. b Examination of mitochondrial membrane integrity, with the JC-1 probe in control and treated OE21 and KYSE450 cell lines, revealed significant mitochondrial depolarization following 48 hour treatment with 5-FU in apoptotic competent OE21 cells, while KYSE450 cells do not exhibit membrane depolarization. Percentages denote the proportion of cells with depolarized mitochondria after a 48 hour incubation with 5-FU, with similar results observed with cisplatin (data not shown). c Morphological features of OE21 cells, treated with 5-FU alone (upper right) are compared to cells that were pre-treated with zVAD-fmk (25 µM) for 2 hours prior to 5-FU treatment (lower right). Analysis revealed that the induced apoptosis (arrows) by 5-FU was completely inhibited by zVAD-fmk (lower right) resulting in a switch to a non-apoptotic morphology (arrowheads). d The extent of apoptotic (clear bars) and non-apoptotic (hatched bars) cell death for each concentration of 5-FU (25-75 µM) in the absence or presence of zVAD-fmk (25 µM), was determined by counting three fields of view per slide, with an average of ~100 cells per field.

Typical markers of apoptotic cell death were examined in all cell lines. Both drug sensitive (OE21/OE33) cell lines displayed active caspase-3, and mitochondrial depolarization in response to 5-FU and cisplatin (FIG. 2a/b). In contrast, the more drug resistant (OE19/KYSE450) cell lines do not show caspase-3 activity or mitochondrial membrane depolarization (FIG. 2a/b).

Evidence for Autophagy in Drug Treated Esophageal Cancer Cells

Figure 3:
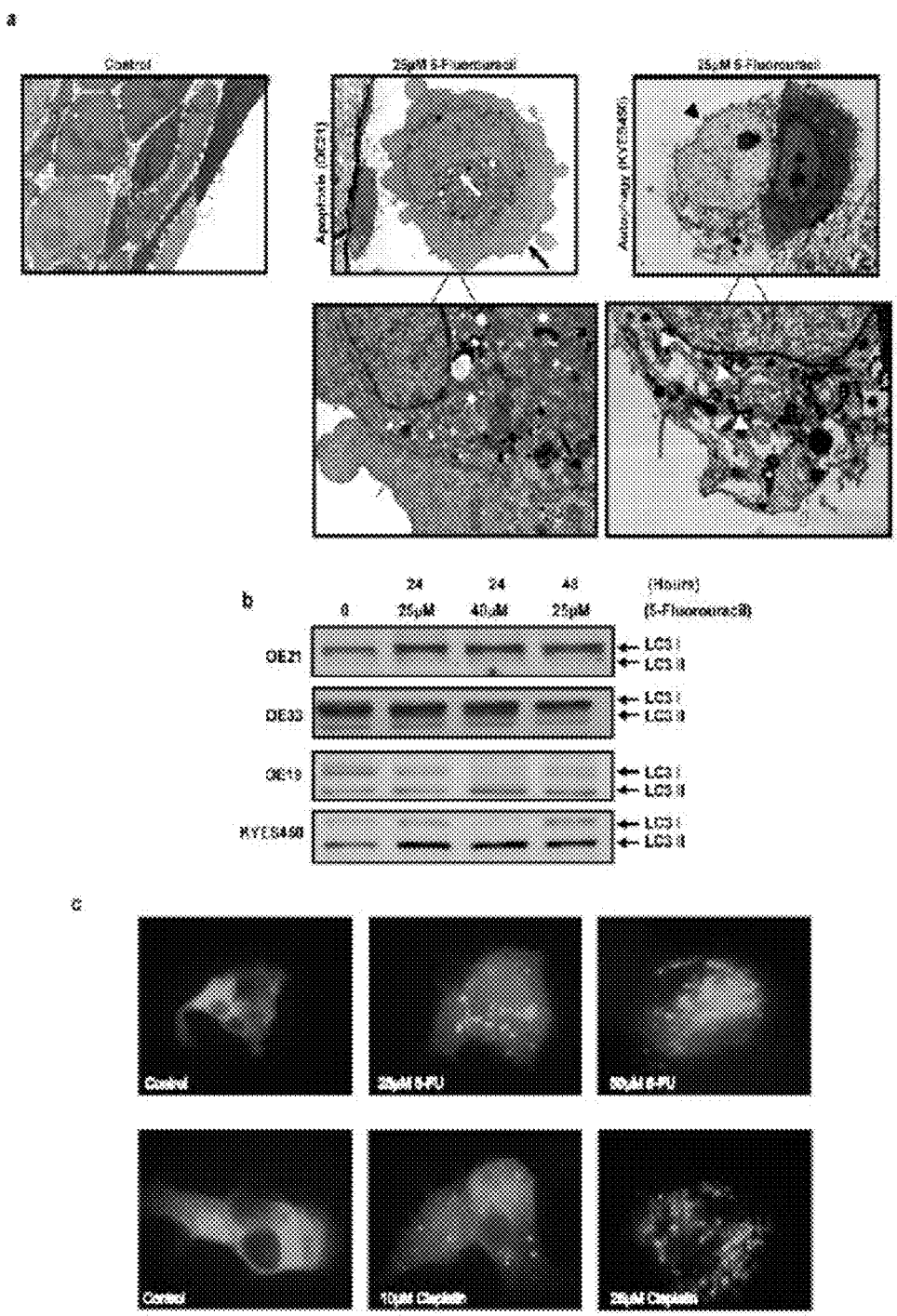
FIG. 3 Analysis of esophageal cells by electron microscopy and LC3 isoform and distribution following drug treatment. OE21 and OE19 cells were incubated with 5-FU (25 µM) for 48 hours. a shows representative electron microscopic images of vehicle control OE21 cells (upper left) and 5-FU treated OE21 (upper middle) and OE19 (upper right) cells. Apoptotic features displayed by OE21 cells, include marginalization of the nucleus (upper middle, white arrow), and an intact cytoplasmic membrane, with surface blebbing (upper middle, black arrow), clear also at a higher magnification (lower left). Non-apoptotic features observed in representative images of OE19 treated cells include apparent disintegration of the plasma membrane (upper right, black arrowhead), an intact nuclear membrane (lower right, white arrowheads), and the emergence of numerous cytoplasmic vacuoles (lower right, white arrowhead). For each treatment or control group, transmission electron microscope images were randomly chosen, from a field of at least 100 cells. b Cells expressing a green fluorescent protein (GFP)-LC3 plasmid, were cultured with 5-fluorouracil (5-FU) (25/40 µM), and/or cisplatin (10/25 µM) for 24 and 48 hours, and analyzed by Western Blot with anti-LC3. Soluble LC3 I is detected at 43 kDa, while autophagosome specific LC3 II at 45 kDa. c GFP-LC3 staining patterns were analyzed by fluorescence microscopy. OE19 vehicle control cells (upper/lower left) display diffuse GFP-LC3 distributed throughout the cytoplasm. 5-FU (25 & 50 µM) (upper middle & right) or cisplatin (10 & 25 µM) (lower middle & right) respectively, show bright punctate patterns of GFP-LC3 fluorescence. These images are representative of two independent experiments.

Ultra structural features of OE21 cells (determined by electron microscopy), incubated with 5-FU, reveal morphological changes consistent with classical apoptotic cell death including marginalization of the nucleus, with an intact but blebbing plasma membrane (upper middle FIG. 3a). In contrast, OE19 treated cells retain an intact nuclear membrane with a distinct nucleolus, and the nuclei have areas of more electron dense heterochromatin. In addition, numerous cytoplasmic vacuoles are evident, many of which appear to surround cytoplasmic material and components, such as the mitochondria, resembling nascent autophagosomes (upper/lower right FIG. 3a). The expression and processing of GFP-LC3 was examined and Western Blot analysis showed no induction of a lower autophagosome-associated LC3II-band in treated OE21/OE33 cells (FIG. 3b). In contrast, a significant increase in LC3II levels are evident in OE19 and KYSE450 cells, following treatment with 5-FU at 24 hours (FIG. 3b). Redistribution of GFP-LC3 from a diffuse cytosolic to a punctate autophagosome-associated pattern, is observed in OE19 (FIG. 3c) and KYSE450 (data not shown) cells following treatment with 5-FU & cisplatin. Diffuse cytoplasmic localization of GFP-LC3 was observed in OE21 and OE33 cell lines, in response to both chemotherapeutic drugs (images not shown).

Figure 4:
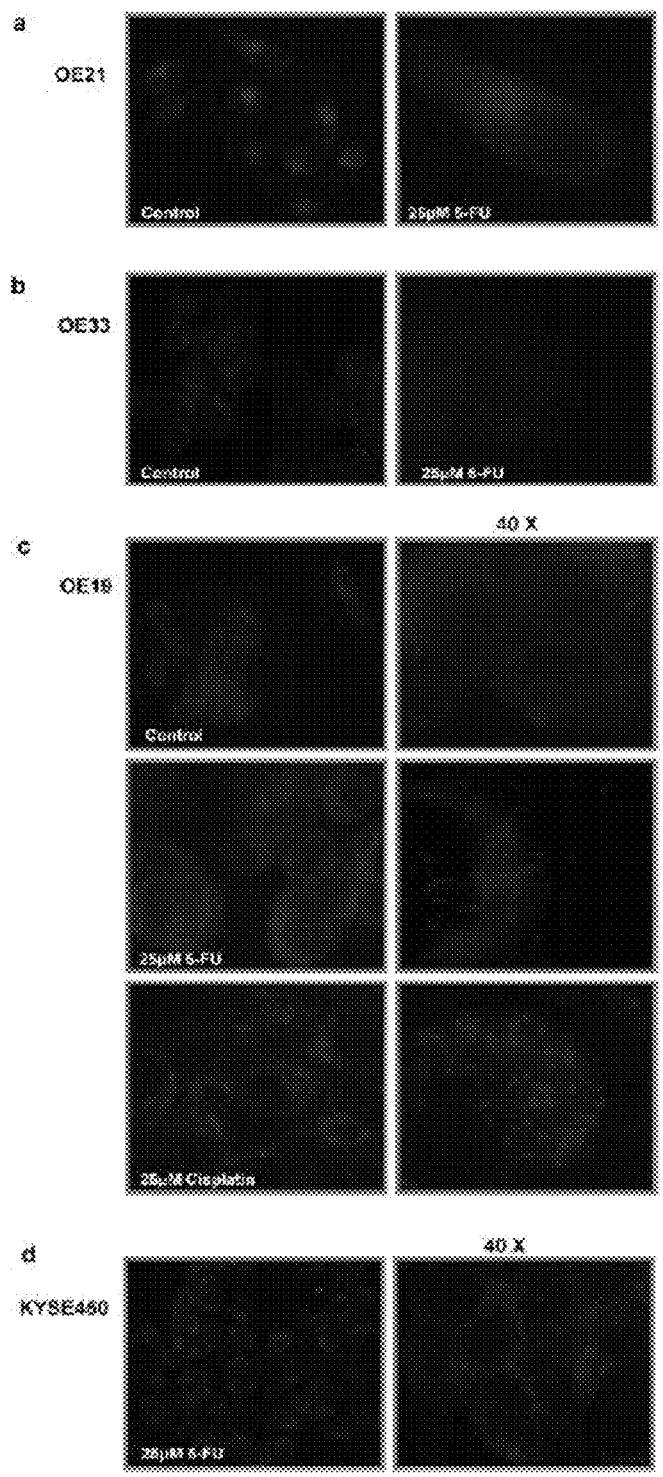
FIG. 4 Visualization of MDC-labelled vacuoles in oesophageal cells. Labelling of the autophagolysosome, with the autofluorescent monodansylcadaverine (MDC) dye, is indicative of autophagy (Munafo and Colombo, 2001, Niemann et al., 2000). This figure shows representative images of a OE21 control and 5-FU (25 µM) treated cells, b OE33 control and 5-FU (25 µM) treated cells. c OE19 vehicle control, 5-FU (25 µM) and cisplatin (25 µM) treated cells (all left panels), with a higher magnification of each image shown in the corresponding right panels. d 5-FU (25 µM) treated KYSE450 cells, with a higher magnification shown in the right panel. Autophagic vacuoles, a feature of Type II cell death, are identified by the accumulation of MDC (bright blue punctate staining) throughout the cytoplasm as observed in the more drug resistant OE19 and KYSE450 cell lines, in response to either 5-FU or cisplatin. The majority of treated cells display MDC punctate staining (developing autophagosomes), yet a percentage of cells will also demonstrate a more diffuse pattern of staining, in all treatment groups. Alternatively, in the absence of acidic autophagic compartments, MDC staining patterns are diffuse, as shown in OE21 and OE33 cells in response to either chemotherapeutic drug. The labeling of a fluorescent region immediately adjacent to the nucleus is typical of the recycling endosome and trans-Golgi network. Images are representative of at least five independent experiments.

Monodansylcadaverine (MDC) dye was also employed to assess levels of mature autophagic vesicle formation in all esophageal cell lines following drug treatment. OE21/OE33 cells failed to develop a punctate staining pattern, in contrast, the more drug resistant, autophagic, OE19 and KYSE450 cell lines demonstrate bright blue punctate staining in response to both chemotherapeutic drugs, consistent with accumulation of MDC in acidic vesicles (FIG. 4). These results collectively suggest that the cytoplasmic vesicles that develop following incubation with either 5-FU or cisplatin, in the OE19 and KYSE450 cells are predominantly autophagosomes.

Figure 5:
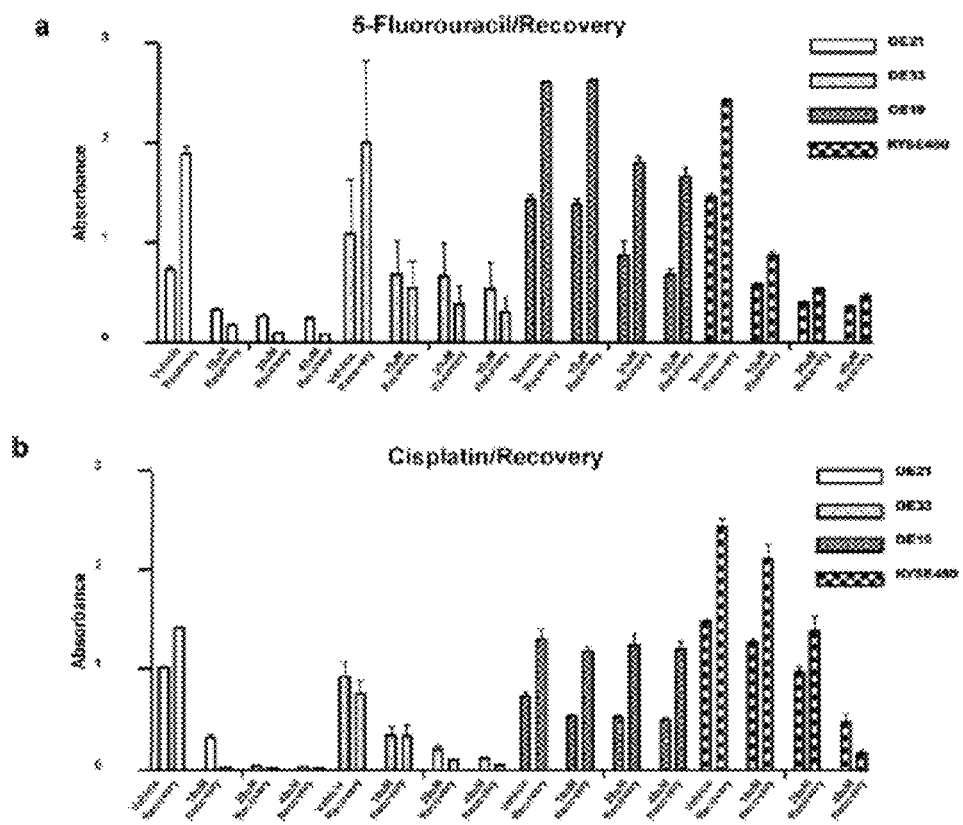
FIG. 5 Recovery of esophageal cancer cells following drug removal. Esophageal cell lines were treated with 5-fluorouracil (5-FU) (10-40 µM) (a) and/or cisplatin (10-40 µM) (b) for 48 hours, and viability of each cell line was determined using the MTT assay. At 48 hours post treatment, in replicate plates (identical seeding & treatment times), culture medium was removed and replaced with fresh medium, and these cells were cultured for a further 48 hours, after which time the MTT assay was repeated. Assays were performed in quadruplicate and results are presented as means and S.E.M (error bars) of absorbance readings.

The Induction of Autophagy in Esophageal Cancer Cell Lines is Associated with the Ability of the OE19 and KYSE450 Cell Lines to Recover, Following the Removal of Drugs As the autophagic process is associated with survival, we examined whether the cell population had the ability to recover, following drug removal. Cells were treated with 5-FU/cisplatin and viability was determined. When recovery was assessed, both OE19 and KYSE450 cell lines demonstrate a remarkable ability to recover and cell cultures are re-populated following even high dose (40 µM) treatment (FIG. 5a/b). The apoptotic competent cell line OE21 fails to recover from low drug doses, and the OE33 cells show minimal recovery. OE19 and KYSE450 cells display morphological features of autophagy when recovering (data not shown). This is the first demonstration that the induction of autophagy, in response to chemotherapeutic agents, has been associated with recovery from drug treatment. While Type II cell death is present (FIG. 1c), sufficient cells seem capable of recovery when the cytotoxic insult is removed.

Figure 6:
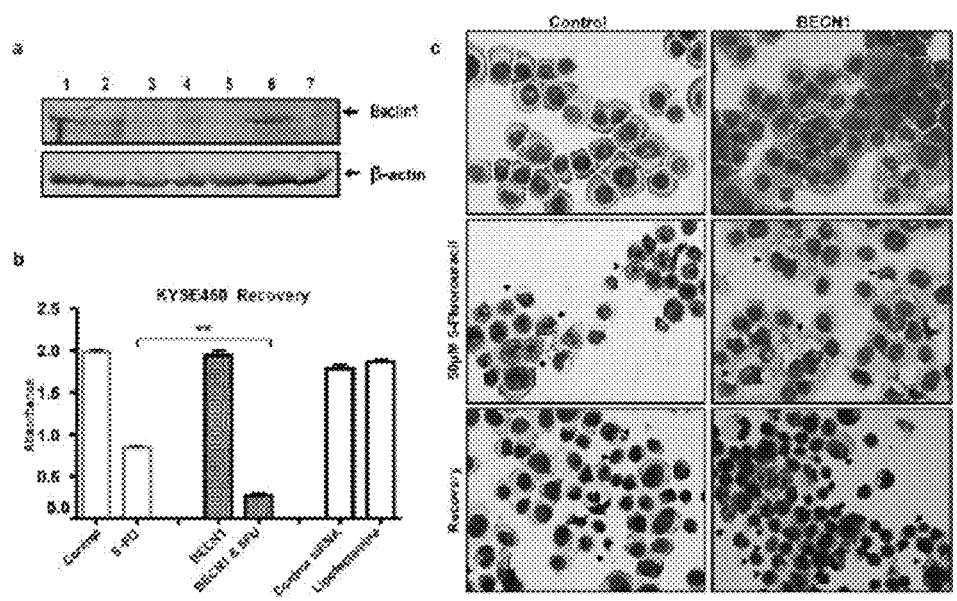
FIG. 6 The effects of inhibiting autophagy by silencing Beclin1, on recovery and morphology of drug treated cells. a Western blot analysis of Beclin1 levels confirm Beclin1 silencing in the KYSE450 cells. Lane 1: control, lane 2: scrambled siRNA, lane 3: 24 hour post transfection, lane 4: 48 hour post transfection, lane 5: 48 hour post transfection & 5-FU (24 hours), lane 6: 50 µM 5-FU alone/no siRNA (48 hours), lane 7: 72 hour post transfection. Knockdown is achieved at 24 hours (lane 3) and maintained for up to 72 hours (lane 7). Untransfected cells (lane 1) and cells transfected with a non-specific siRNA (lane 2) serve as controls. β-actin detection serves as a loading control. b MTT assay was used to assess the effect of Beclin1 knockdown (BECN1), on recovery (96 hours post drug treatment) of KYSE450 cells, following 48 hour incubation with 5-FU (50 µM). Values represent the Mean absorbance+/−S.E.M (error bars) of three independent experiments. Asterisks indicate where the 5-FU treated cells, in which Beclin1 is silenced, are statistically different from 5-FU treated cells (**p<0.005, *p<0.05) (paired t-test). c Shows morphological analysis of KYSE450 cells untransfected (control) and transfected with siRNA (BECN1), treated with 5-FU (50 μM) for 48 hours (middle panels). Morphological features of recovered KYSE450 cells (96 hours post treatment), without and with Beclin1 silencing are shown in the lower left and right panels respectively (FIG. 4c). Autophagic morphology is depicted with arrowheads. Experiment is representative of at least three similar experiments.

To assess whether autophagy contributed to this recovery, autophagy was inhibited by depleting the key regulator, Beclin1 with short interfering RNA (siRNA). A complex containing Beclin1, a class III PI3-kinase (hVps34) and other cofactors initiates the formation of the autophagosome (Liang et al., 1999, Levine et al., 2008, Pattingre et al., 2008), and is critical for autophagic survival (Qu et al., 2003). Beclin1 silencing (maintained for 72 hours, FIG. 6a) attenuated the ability of KYSE450 cells to recover (96 hours recovery) from a 48 hr treatment with 5-FU (FIG. 6b).

Beclin1 silencing clearly reduced autophagic survival, yet autophagic/Type II cell death was unaffected. There was no elevation of necrosis or apoptosis in 5-FU treated cells with Beclin1 silencing (FIG. 6c middle right) compared to cells treated with 5-FU alone (middle left). Both display a highly vesicular cytoplasm (arrowheads), typical of Type II cell death. Morphology of populations following drug withdrawal (lower right) also show that transfected cells fail to recover, compared to cells treated with 5-FU alone (lower left—many cells regaining cytoplasmic material). These data suggest that the induction of Beclin1-dependent autophagy, in response to chemotherapeutic drugs, contributes to recovery, when drugs are withdrawn. However, Beclin1 is dispensable for autophagic/type II cell death (arrowheads).

Figure 7:
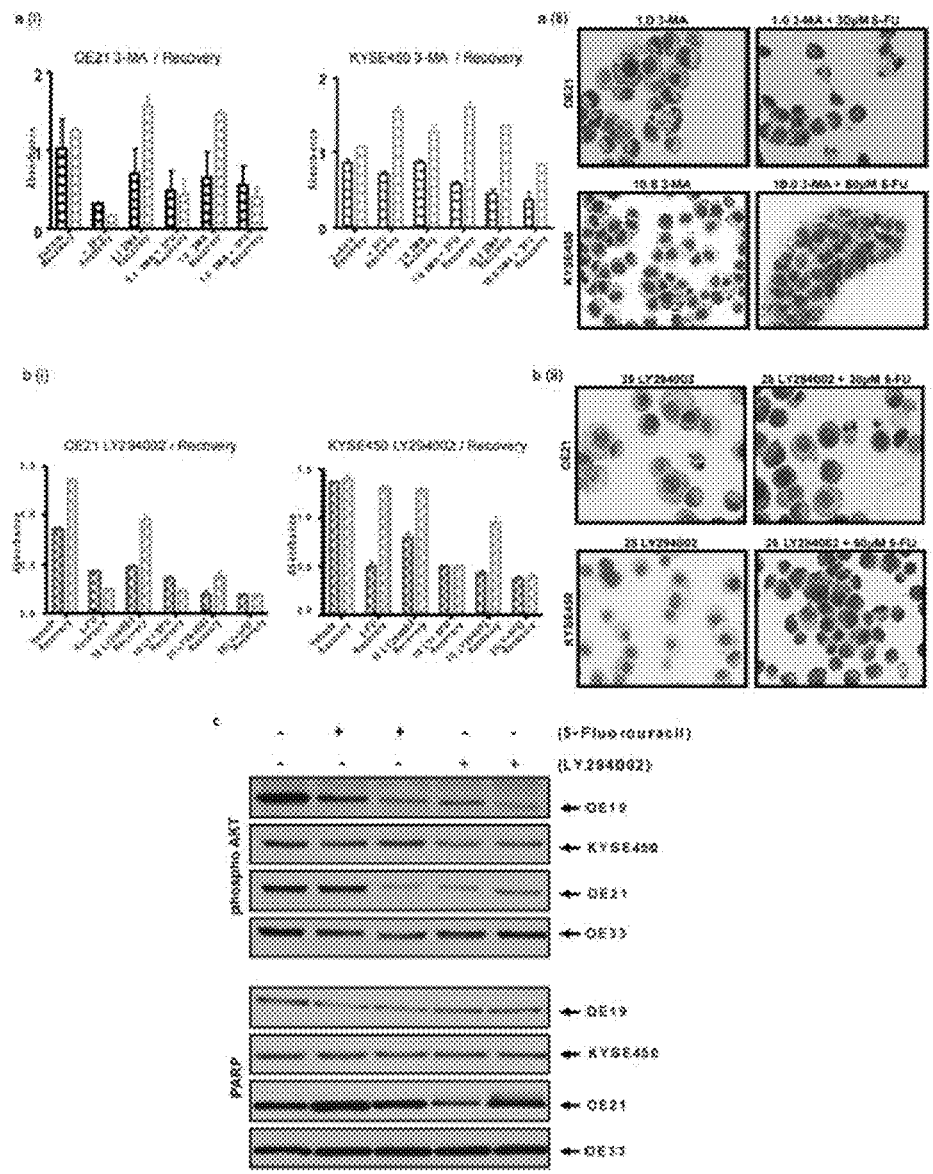
FIG. 7 Effects of autophagy inhibitors, 3-Methyladenine (3-MA)/LY294002 and 5-FU combination treatment on morphology and recovery of oesophageal cells. a(i) OE21 and KYSE450 cell lines were treated with 3-MA (0.1-10.0 μM) without and with 5-fluorouracil (30/50 μM) for 48 hours and viability was assessed using the MTT assay. Recovery data was acquired 48 hours after drug removal. Both cells lines (OE21 (0.1-1.0 μM) and KYSE450 (1.0-10.0 μM)) recover from treatment with 3-MA alone. Combination treatments of 3-MA (0.1-1.0 μM) and 5-FU did not significantly influence sensitivity or recovery of OE21 or KYSE450 cells. Cytotoxicity was enhanced at the higher concentration of 10 μM 3-MA in KYSE450 cells and recovery was diminished. a(ii) Examines morphological features of OE21 cells following 3-MA treatment without (upper left) and with 5-FU (30 μM) (upper right), following 48 hour incubation. KYSE450 cells were treated with 3-MA (10.0 μM) without (lower left) and with 5-FU (50 μM) (lower right), again for 48 hours. Treatment with 3MA alone did not significantly affect morphology or either cell line (left panels). Pre-treatment with 3-MA enhanced an autophagic morphology in response to 5-FU in both OE21 (upper right) and KYSE450 (lower right) cells. b(i) OE21 and KYSE450 cells were treated with LY294002 (10/25 μM) alone or in combination with 5-FU (30/50 μM respectively), and viability was assessed using the MTT assay. Recovery was measured 48 hours after drug removal. Both cells lines demonstrate recovery from LY294002 (10/25 μM) alone. Combination treatments did not significantly influence sensitivity or recovery of OE21 cells, following drug removal. In KYSE450 cells, combination treatments did not significantly influence sensitivity to 5-FU but the extent of recovery following drug removal was reduced. b(ii) The morphology induced by LY294002 (25 μM) was predominantly autophagic in both OE21 (upper left) and KYSE450 (lower left), with marked cytoplasmic vacuoles observed in both cell lines. When combined with 5-FU (30/50 μM), OE21 cells display both apoptotic and autophagic morphologies (upper right), while KYSE450 cells display enhanced autophagy (lower right) in response to combination treatments. c LY294002 (10/25 μM) reduced phosphorylation of Akt in all four oesophageal cell lines. Cells were incubated with 5-FU or LY294002 and subjected to Western blot analysis with anti-phospho Akt. Lane 1: vehicle control, lanes 2 & 3: 40 μM 5-FU (24/48 hours), lanes 4 & 5: LY294002 10/25 μM for 48 hours. Blots were probed with anti-PARP antibody to demonstrate equal loading.
Figure 8:
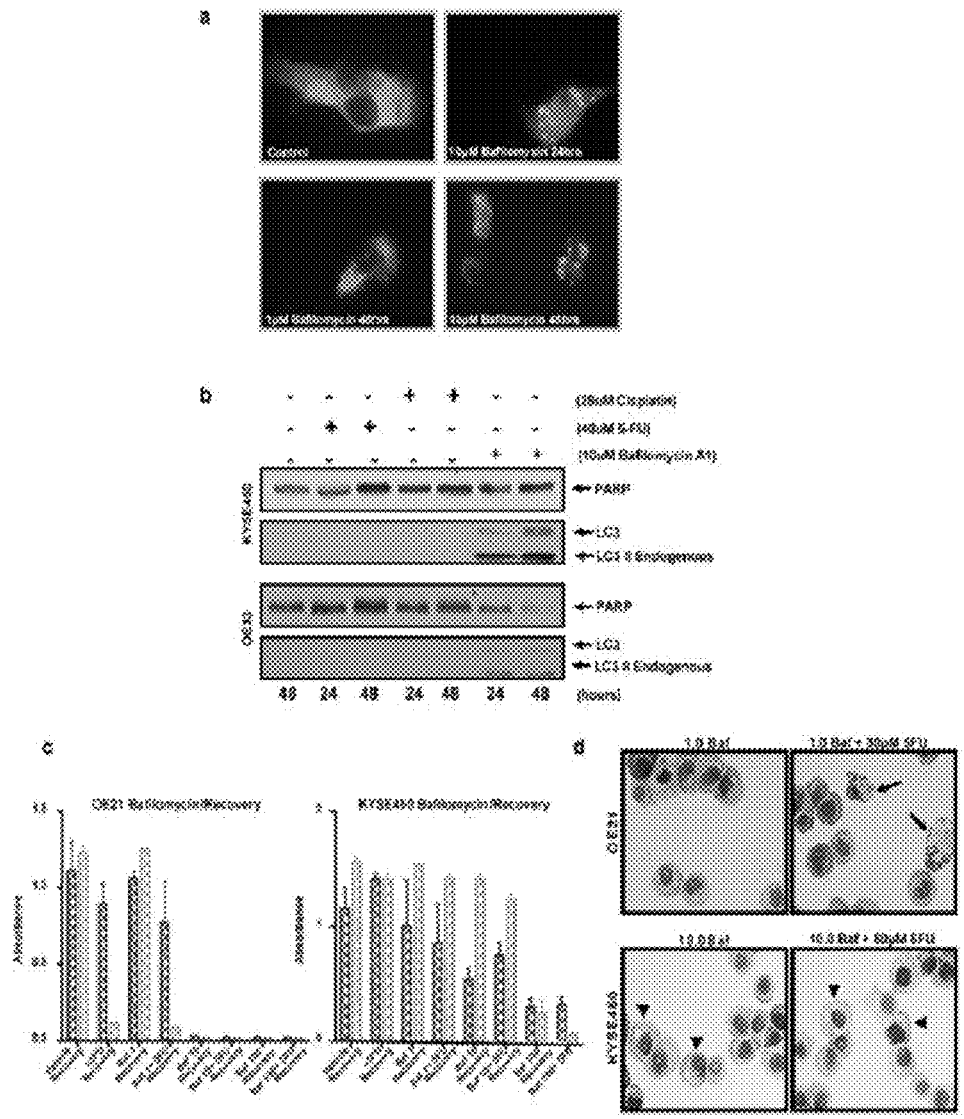
FIG. 8 Effect of inhibiting autophagosome processing with BafilomycinA1 (Baf) alone and in combination with 5-FU, on cell viability and morphology. a To confirm the proposed inhibitory action of Bafilomycin A1 (which prevents the fusion of the autophagosome to the lysosome), OE19 cells expressing a GFP-LC3 plasmid were cultured in the presence of 10 nM bafilomycinA1 for 24 and 48 hours. Examination of GFP-LC3 distribution following treatment revealed a diffuse cytoplasmic distribution of LC3 in vehicle control cells, with a BafilomycinA1 induced accumulation of GFP-LC3 tagged autophagosomes, seen as a bright punctate pattern at 24 (10 nM) and 48 hours (1/10 nM). Images are representative of three individual experiments. b BafilomycinA1 (10 nM) induced an accumulation in the levels of endogenous LC3 in both KYSE450/OE33 oesophageal cells, 24 and 48 hours post treatment, as determined by Western blot analysis. Lane 1: vehicle control, lanes 2 & 3: 40 μM 5-FU (24/48 hours), lanes 4 & 5: 25 μM cisplatin (24/48 hours), lanes 6 & 7: 10 nM bafilomycinA1 (24/48 hours). c The effects of bafilomycinA1 alone (1, 10,100 nM) or in combination with 5-FU (30/50 μM) on viability were assessed using MTT assay. Treatment with 10 and 100 nM Bafilomycin (without or with 5-FU) induced significant cell death in the OE21, from which they cannot recover. KYSE450 cells show a reduction in MTT with Bafilomycin treatments (10-100 nM), but will recover from 10 nM. Combination treatments in the KYSE450 cells do not alter their susceptibility to 5-FU, or affect their ability to recover except at 100 nM Bafilomycin which is cytotoxic alone. d Examination of the morphological features of Bafilomycin treatment revealed that, on its own Bafilomycin induced significant levels of vesicular accumulation due to inhibition of endogenous autophagy in OE21 (Bafilomycin 1.0 nM) (upper left) and KYSE450 (Bafilomycin 10.0 nM) (lower left) cells. When combined with 5-FU (30 μM), OE21 cells exhibit both autophagy and apoptosis, and both morphologies can be identified in the same cells (DNA fragmentation with extensive cytoplasmic vacuolization) (upper right; arrows). In KYSE450 cells, combined treatment with Bafilomycin and 5-FU (50 μM) (lower right) enhanced the autophagic morphology of these cells (arrowheads).

Modulation of chemo-sensitivity and recovery in OE21 and KYSE450 cells by pharmacological inhibitors 3-MA and LY294002 was examined (FIGS. 7a & b). PI-3kinase inhibitors do not inhibit autophagy in these cells. In KYSE450 cells, autophagy and type II morphologies are enhanced in combination treatments with 5-FU and PI-3kinase inhibitors (3-MA and LY294002). Recovery is also reduced at higher concentrations of inhibitors. Addition of bafilomycin does not significantly enhance cytotoxicity (FIG. 8), however the inhibition of autophagosome/lysosome fusion elevates vesicular content in all cells and provides striking evidence of autophagy in apoptotic cells.

Assessment of Lithium Chloride and 5-FU Combination Treatments

Figure 9:
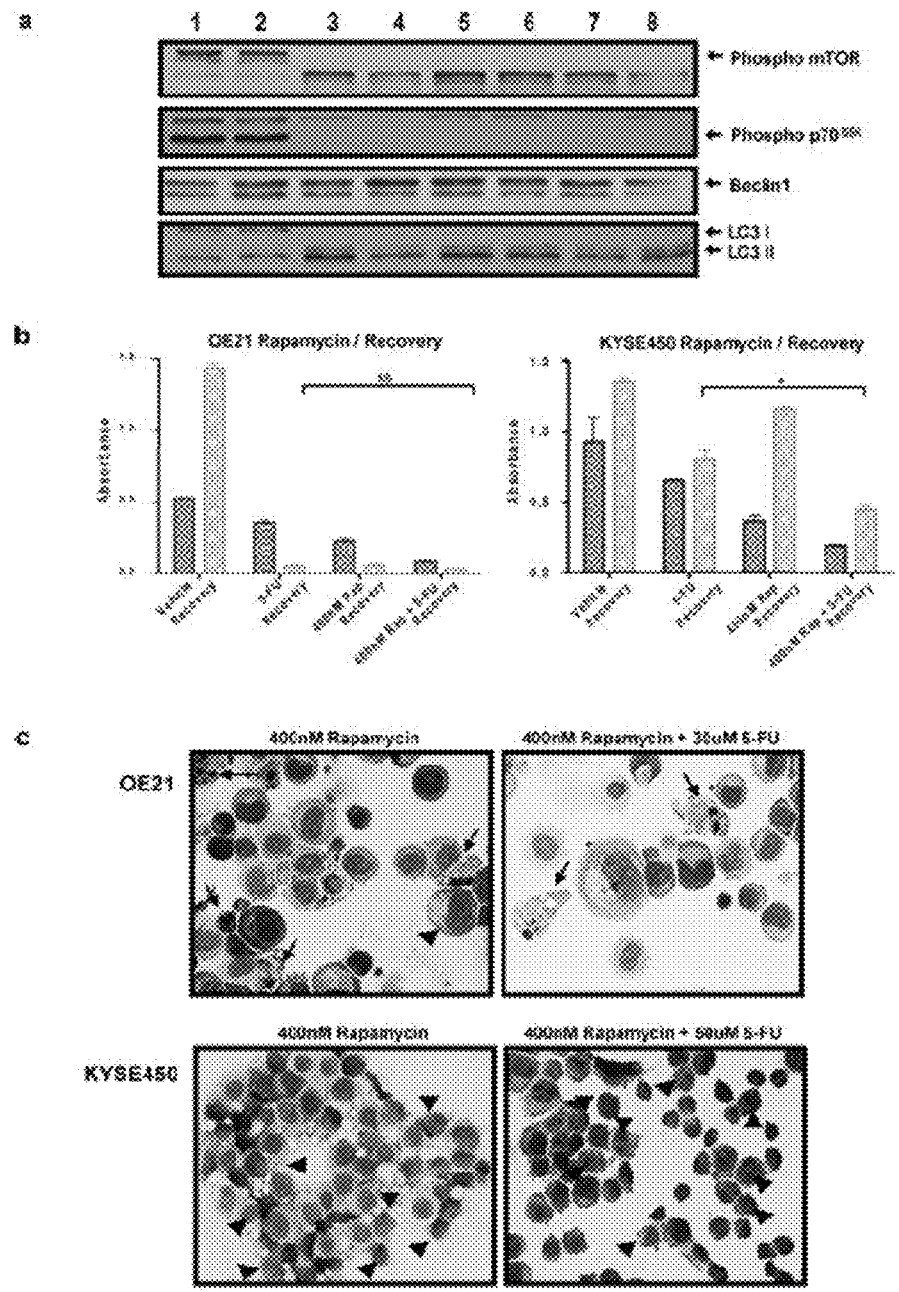
FIG. 9 Effect of Rapamycin and 5-FU combination treatment on recovery and morphology of oesophageal cells. a To confirm the proposed inhibitory action of rapamycin on mTOR, KYSE450 cells were incubated with combinations of 5-FU and rapamycin and the levels of phospho mTOR (anti-phospho-mTOR (ser2448)) and its downstream target $p70^{S6K}$ (anti-phospho-$p70^{S6K}$) were examined by Western blot (100 μg/sample). Lane 1: vehicle control, lanes 2 & 3: 50 μm 5-FU 24/48 hours, lanes 4, 5 & 6: 200 nM rapamycin, with the addition of 5-FU for 24/48 hours (lanes 5 & 6); lane 7: 400 nM rapamycin, with the addition of 5-FU for 48 hours in lane 8. Rapamycin was added two hours prior to 5-FU in combination treatments, otherwise cells were cultured in rapamycin for 48 hours. In addition, cell lysates were analyzed with anti-LC3 and anti-Beclin1, to examine the consequence of inhibition of mTOR on autophagy. Rapamycin treatment reduced levels of phospho mTOR and phospho-$p70^{S6K}$ in KYSE450 cells, and is associated with an induction of LC3 processing and increased levels of Beclin1, indicative of autophagy induction. 5-FU treated KYS450 cells (lane3) display a similar reduction in phospho mTOR/phospho-$p70^{S6K}$ suggesting that autophagy induction by 5-FU (48 hours) in these cells, involves inhibition of the mTOR pathway. The apoptotic competent cells (OE21/OE33) display reduced phospho-mTOR/phospho-$p70^{S6K}$, in response to rapamycin, yet fail to induce changes in Beclin1 or LC3 II (data not shown). b The effects of rapamycin alone (400 nM) or in combination with 5-FU (30/50 μM) in OE21 and KYSE450 cells was assessed by measuring viability following a 48-hour incubation. Recovery data, in this experiment, shows OE21 (& OE33 not shown) cells are susceptible to rapamycin and do not recover. In contrast, OE19/KYSE450 cells will recover following removal of rapamycin alone, suggesting it is an ineffective treatment for apoptotic incompetent cells. Combined treatments with 5-FU accentuates autophagy, reduces recovery, and represents a better treatment approach than either agent alone. Asterisks indicates a significant difference in recovery of KYSE450 cells treated with a combination of rapamycin (400 nM) and 5-FU when compared to 5-FU alone (*p<0.05) (paired t-test). No statistical difference in recovery of OE21 cells were seen when comparing the combination treatment with 5-FU alone (NS). c Morphological analysis of OE21 cells treated with rapamycin (400 nM) without and with 5-FU (30 µM) shows that rapamycin alone induces a predominant apoptotic cell death response, which when combined with 5-FU resulted in a mixed morphology, with a predominance of apoptotic cell death. c KYSE450 cells treated with rapamycin (400 nM) without and with 5-FU (50 µM) reveal the induction of autophagy with single agent treatment. The combined treatment enhanced this morphology in both KYSE450 (right) and OE19 (data not shown). Apoptotic cell death is shown with arrows and autophagic morphology with black arrow heads.

As specific inhibitors of autophagy are not currently available, the acceleration of autophagy beyond a survival process, into autophagic cell death was examined as potential therapeutic approach. The effects of two known autophagy inducers Rapamycin and Lithium chloride (LiCl) were assessed for drug sensitivity and recovery of esophageal cancer cells (Rapamycin data is included as FIG. 9). Evidence suggests that LiCl inhibits inositol monophosphatase, with a reduction in inositol-1,4,5-triphosphate ($IP_3$) levels (Sarkar and Rubinsztein, 2006), therefore representing an mTOR-independent mechanism of action.

Figure 10:
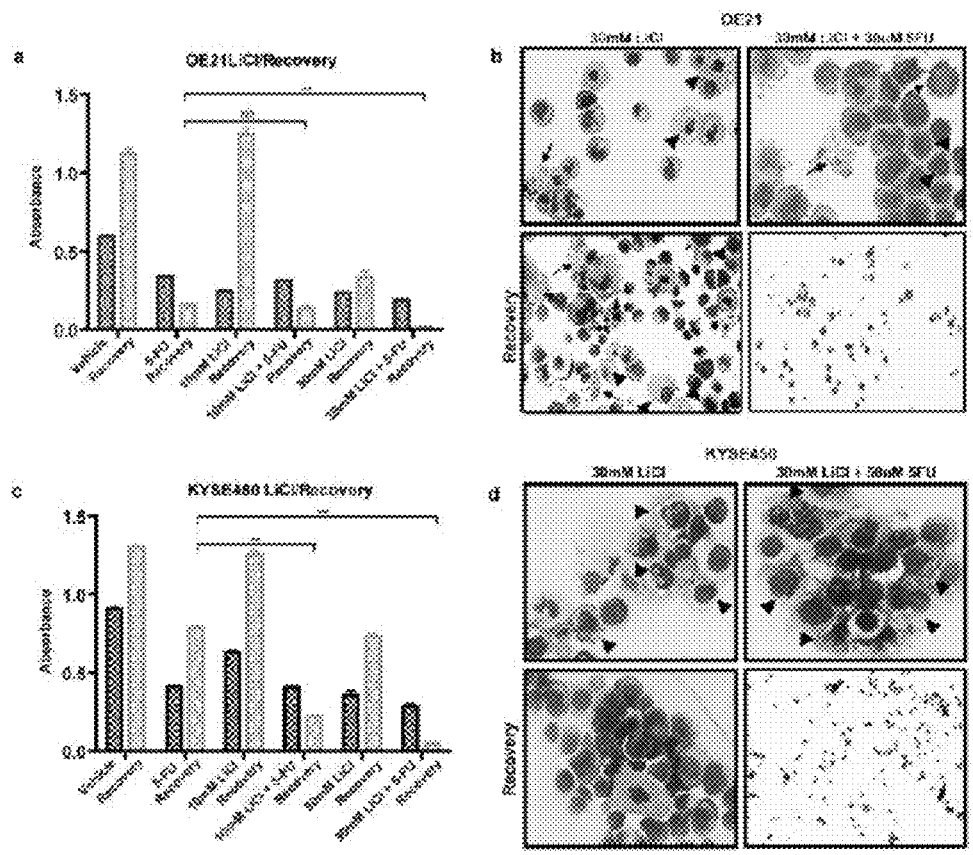
FIG. 10 Consequence of combining lithium chloride (LiCl) with 5-FU, on viability, recovery and morphology of OE21 and KYSE450 cells. The effects of LiCl alone or in combination with 5-FU, in all esophageal cell lines was examined. Cells were treated for 48 hours, with recovery data recorded 144 hours after initial treatment. a Demonstrates the effects of 5-FU (30 µM), LiCl (10/30 mM) or combinations of both on viability/recovery. Asterisks indicates a significant difference in recovery of OE21 cells treated with combination LiCl (30 mM) and 5-FU when compared to 5-FU alone (***p<0.002, *p<0.05) (paired t-test) (ns: not significant). b Representative morphological changes that occur in OE21 cells following LiCl treatment, without (upper left) and with (upper right) 5-FU, with respective recovery (96 hour recovery) shown in lower left/right. c KYSE450 cells were treated with 5-FU (50 µM), LiCl (10/30 mM) or combinations of both and effects on viability/recovery were determined. Asterisks indicates a significant difference in recovery of KYSE450 cells treated with combination LiCl (10 and 30 mM) and 5-FU when compared to 5-FU alone (***p<0.002, *p<0.05) (paired t-test). MTT data is presented as Mean absorbance+/−S.E.M (error bars) of four independent experiments. d Morphology of KYSE450 cells in response to LiCl treatment without (upper left) and with 5-FU (upper right), with corresponding recovery (96 hour recovery) in lower left/right respectively. The magnification of the lower panels in b and lower right panel in d is 10×, all other images are captured at 40×. Apoptotic cell death is shown with arrows, autophagic morphology with black arrowheads and mitotic catastrophe is shown with red arrowheads.

Apoptosis competent-OE21 cells respond to treatment with 10 and 30 mM LiCl alone. Recovery from 10 mM is complete, indicating that MTT reduction is primarily due to a drop in metabolism. At 30 mM, recovery is reduced, but evident (FIG. 10a). A limited recovery in 5-FU treated OE21 cells is apparent at this 96 hours recovery period, possibly due to the presence of autophagic cells as a minor population (7%) (FIG. 1c), which have the potential to recover. A combined LiCl and 5-FU treatment eliminated these recovering cells. LiCl (FIG. 10b upper left) induced mixed morphologies-autophagic and apoptotic in OE21 cells, present also in recovering populations with the appearance of some large cells displaying morphology previously described as mitotic catastrophy (lower left, red arrow head). Combination treatments resulted in predominantly apoptotic morphology, with many shrunken nuclei (upper right). Similar responses were observed in the OE33 cell line (data not shown).

KYSE450 cells respond to LiCl treatment alone (48 hour), followed by extensive recovery at 96 hours. However, when 30 mM LiCl is combined with 5-FU, all cells fail to recover, even after 96 hours (FIG. 10c). LiCl alone induced an autophagic morphology (FIG. 10b arrowheads), which was greatly enhanced by the addition of 5-FU (upper right). Morphology confirms that KYSE450 cells recover from LiCl alone (lower left), however cells treated with both LiCl and 5-FU fail to recover (lower right). This is the first drug combination to which these resistant cells were completely susceptible.

The BH3 Mimetic, HA14-I Enhanced the Cytotoxicity of 5-FU in KYSE450 Oesophageal Cells.

Figure 11:
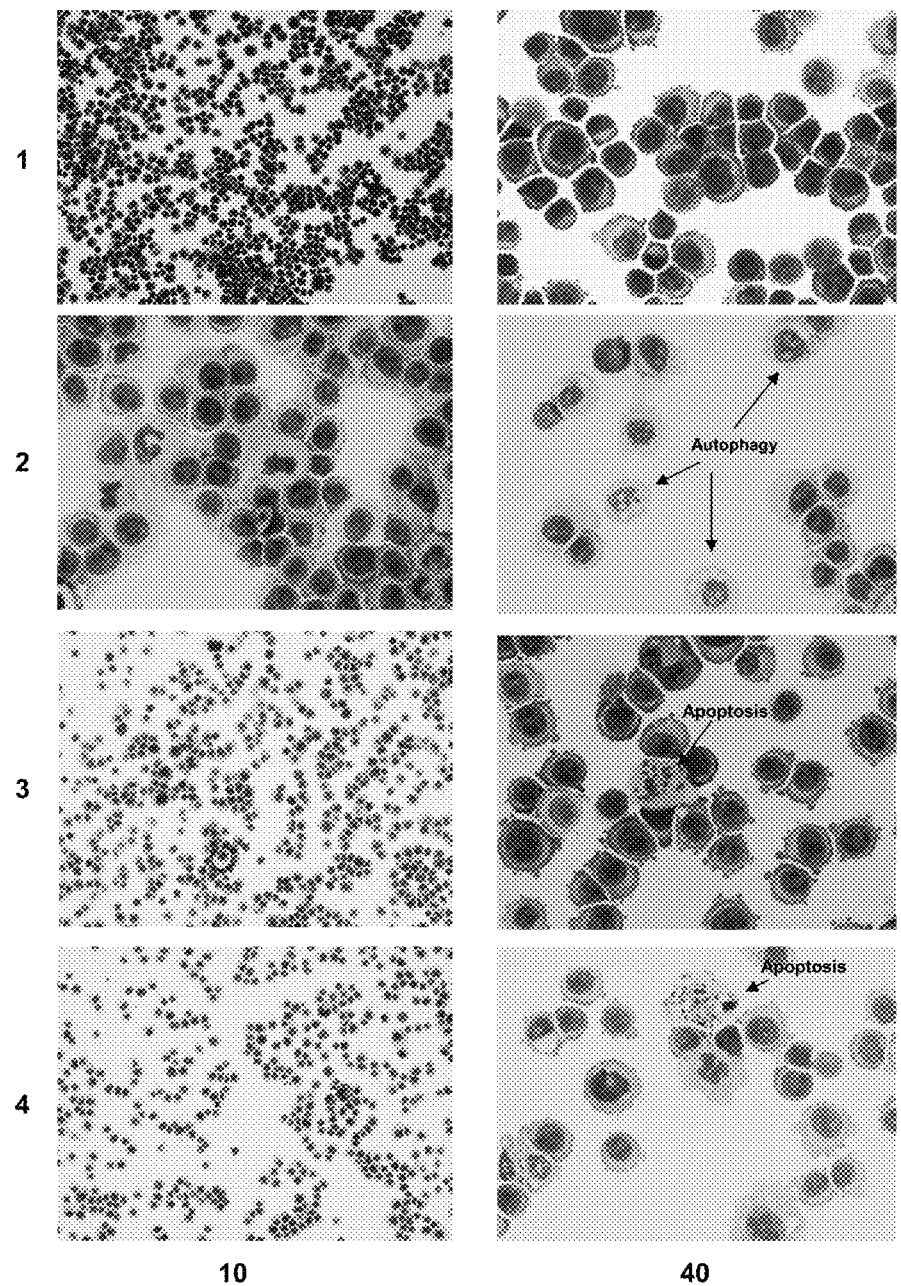
FIG. 11 Effects of combining 5-FU and BH3 Mimetic HA14-1 on the morphology of KYSE450 cells. Morphological analysis of KYSE450 cells following exposure to 5-FU (50 µM) and HA14-1 (5 µM) for 24 hours, examined at 10× and 40× magnification. 1 Untreated cells. 2 5-FU exposure for 24 hours causes autophagic phenotype (shown in image) 3 HA14-1 exposure for 24 hours rarely causes apoptosis (shown in image) 4 Combined 5-FU and HA14-1 treatment rarely causes apoptosis (shown in image).
Figure 12:
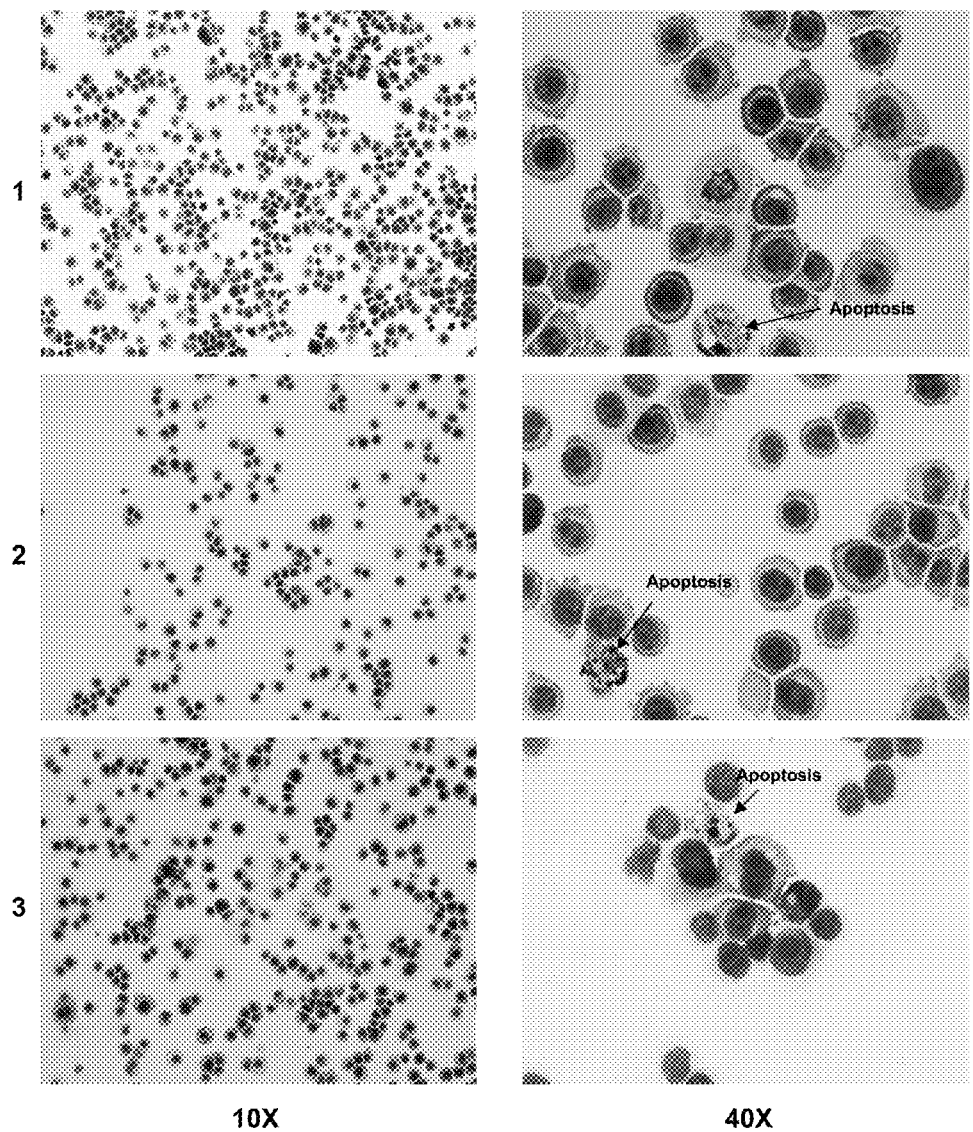
FIG. 12 Effects of combining 5-FU and HA14-1 on the morphology of KYSE450 cells Morphological analysis of KYSE450 cells following exposure to 5-FU (50 µM) and HA14-1 (10 µM/20 µM) for 24 hours, examined at 10× and 40× magnification. 1 HA14-1 (10 µM) for 24 hours. 2 HA14-1 (10 µM) and 5-FU exposure for 24 hours rarely causes an apoptotic phenotype (shown in image) 3 HA14-1 (20 µM) exposure for 24 hours rarely causes apoptosis (shown in image).
Figure 13:
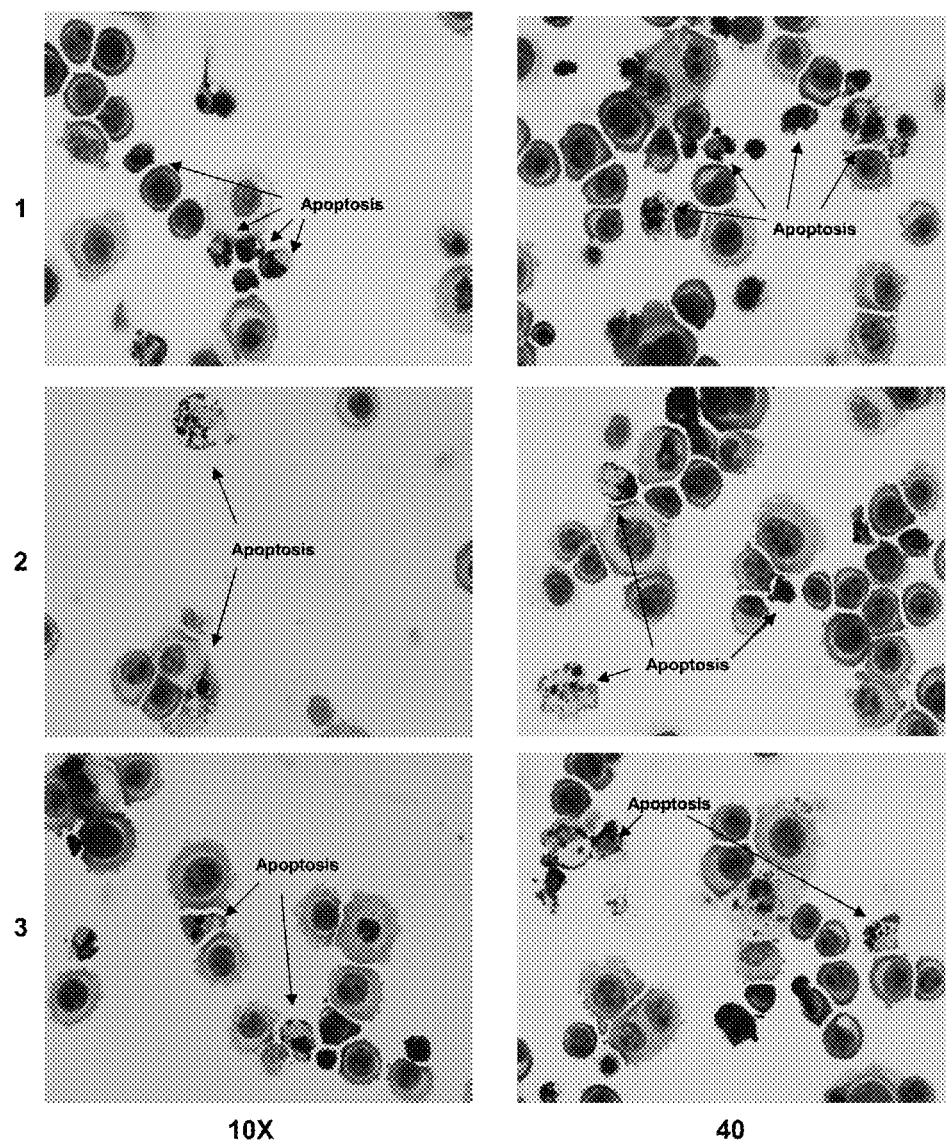
FIG. 13 High concentration of HA14-1 induces apoptosis in KYSE450 Morphological analysis at 40× magnification of KYSE450 cells following exposure to HA14-1 (30 µM) for 24 hours, apoptotic cells are visible (examples shown on each image).
Figure 14:
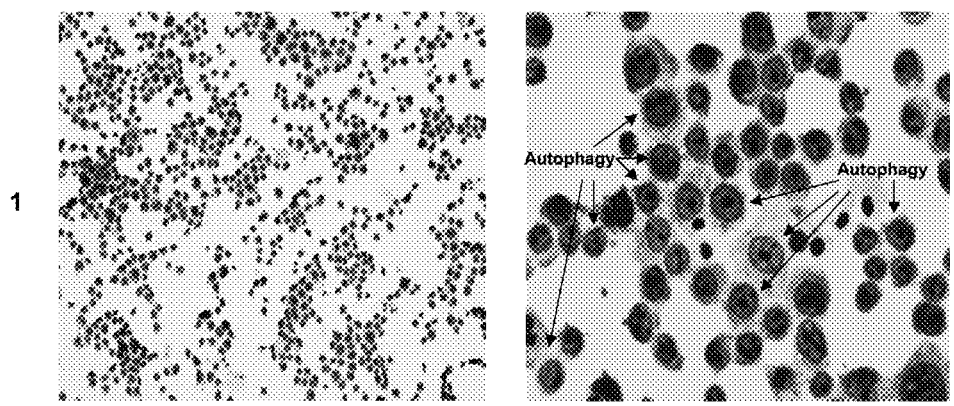
FIG. 14 Combined treatment of 5-FU and HA14-1 induces an autophagic phenotype. KYSE450 cells were treated for 48 hours with HA14-1 (20 µM) and 5-FU (50 µM), 48 hours post treatment the cells displayed an autophagic phenotype (examples shown on image).
Figure 15:
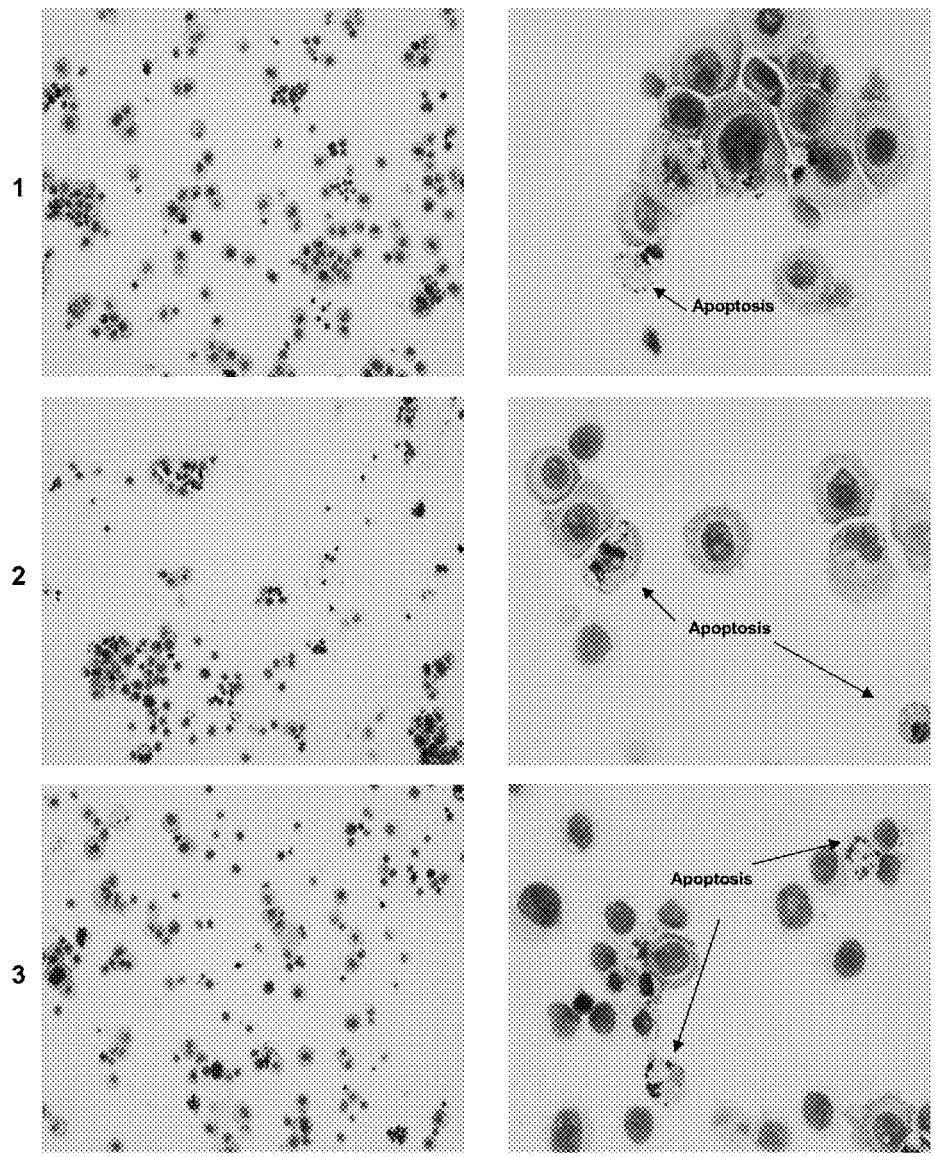
FIG. 15 High concentration of HA14-1 induces apoptosis in KYSE450 cells. Morphological analysis at 10× and 40× magnification of KYSE450 cells following exposure to HA14-1 (30 µM) for 48 hours, apoptotic cells are visible 48 hours post treatment (examples are shown on each image)
Figure 16:
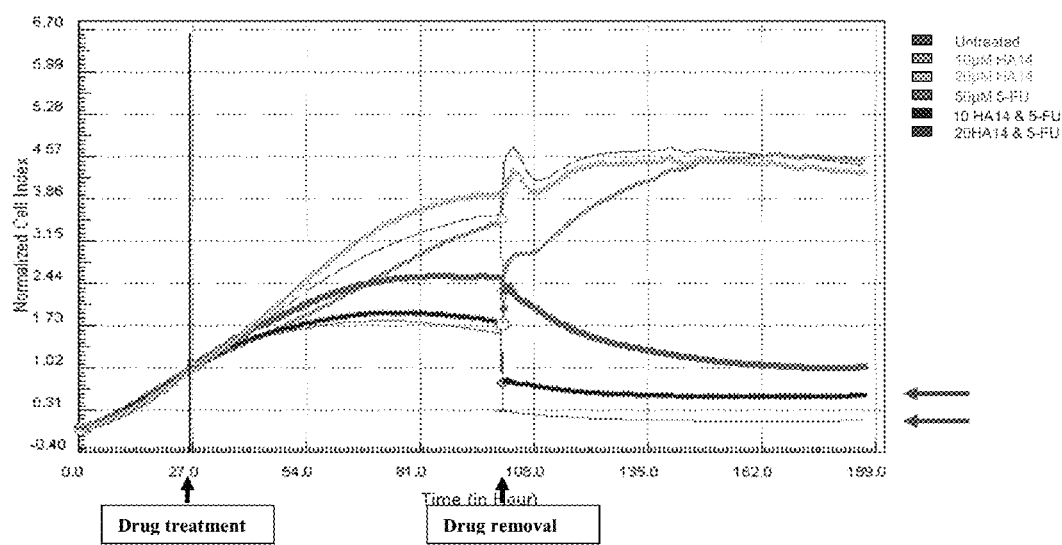
FIG. 16 Effect of 5-Fluorouracil (5-FU) and BH3 Mimetic HA14-I on viability in KYSE450 cells. KYSE450 cells were treated for ~80 hours with HA14-I (10 and 20 µM), 5-FU (50 µM) and combinations of both HA14 & 5-FU. Following treatment, all drugs were removed and cells were allowed to recover for an additional 85 hours. Cell growth and viability were monitored with the Real-Time Cell Analyzer (Roche). Cytotoxicity, due to 5-FU, is enhanced in the presence of BH3 mimetic (HA14-1) (2 dark blue lines, 2 red arrows).

The sensitivity of the KYSE450 oesophageal cells was evaluated in response to the BH3 mimetic, HA14-I (5-30 µM) alone and in combination with 5-FU (50 µM). Morphological analysis demonstrated that 24 hours post treatment, at the lowest concentration of HA14-I (5 µM) without and with 5-FU (FIGS. 11 (3) and (4) respectively), the induction of apoptosis is observed, but at very low levels. Likewise, with 10 µM HA14-I, without and with 5-FU (FIGS. 12 (1) and (2)) and with 20 µM HA14-I (FIG. 12 (3)), the induction of apoptosis is apparent, but again at low levels. At 48 hours post treatment, the lower concentrations of HA14 in combination with 5-FU (FIG. 14 (1)) induces a non-apoptotic/Type II morphology (with many of the cells exhibiting loss of cytoplasmic material, no discernable plasma membrane, and pyknosis of the nuclear material), with little or no evidence of apoptosis. The higher concentration of HA14-I (30 µM) alone, however induced clear levels of apoptotic cell death, at both 24 and 48 hours post treatment (FIG. 13 and FIG. 15).

Initial data from the Real-Time Cell Analyzer, monitoring cell growth and viability, suggests that the combination of 10 and 20 µM HA14-I & 5-FU (50 µM), enhanced the cytotoxic effect of 5-FU alone. The corresponding morphology for combination treatments (FIG. 14 (1)), would indicate that this enhanced cytotoxicity is due to the induction of Type II cell death.

Figure 17:
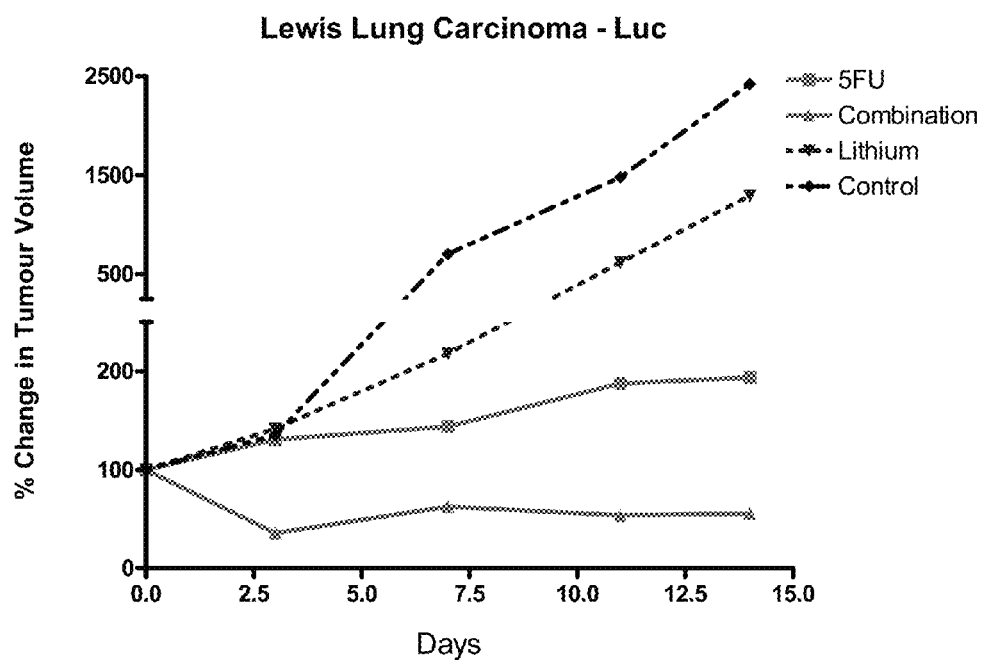
FIG. 17 Antitumour effect of combination therapy of 5-FU and Lithium Chloride on Lewis lung carcinoma derived tumours in a MF1 nu/nu murine model. MF1 nu/nu mice (5 per group) bearing subcutaneous Lewis Lung carcinoma tumours, expressing firefly Luciferase (LLC-Luc), were treated with an intratumoural injection three times a week with PBS (Control), Lithium Chloride (200 mg/kg), 5-FU (20 mg/kg) and a combination of both Lithium and 5-FU (200 mg/kg, 20 mg/kg). Tumour volumes were measured (V=a·b$^2$/6, a=larger diameter, b=smaller diameter) twice weekly and data is presented as percentage change of initial tumour volume.
Figure 18:
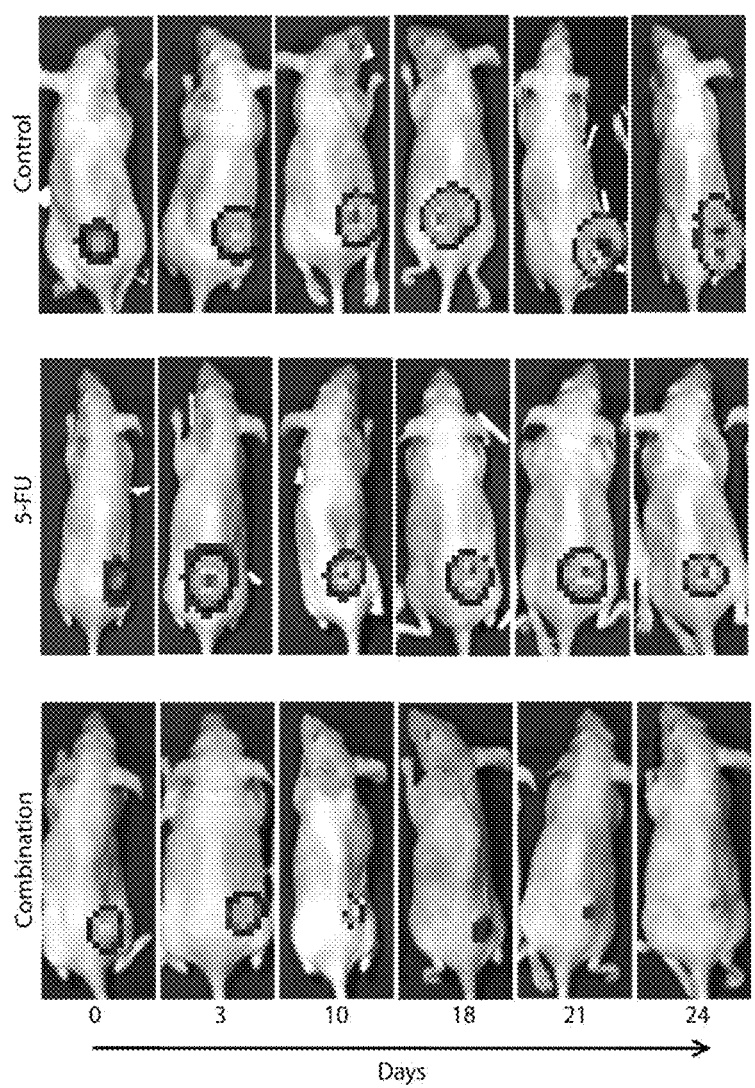
FIG. 18 a. Antitumour effect of combination therapy of 5-FU and Lithium Chloride on Lewis lung carcinoma derived tumours in a MF1 nu/nu murine model. Whole body bioluminescence imaging using the 2D IVIS imaging system of tumour bearing mice was carried out twice weekly, in control (PBS), 5-FU (20 mg/kg) and combination (5-FU (20 mg/kg) & Lithium Chloride (200 mg/kg)) treated mice (three per group). Images of one representative mouse from each group is presented. b Antitumour effect of systemically delivered combination therapy on metastatic disease. Lewis lung carcinoma (Wild type) cells (1×10$^6$ cells) (spontaneously metastasize to the lung) were injected into the right flank of C57 BL adult female mice after anaesthesia. Primary tumours were measured on alternative days following injection of tumour cells using a Vernier Calipers. Tumour diameter was measured and when mean tumour diameters were 8.0 mm+/−0.2 mm (~14 days post injection of tumour cells), primary tumours were excised and animals were randomized into 4 groups (n=10 per group). The treated and control groups received intraperitoneal injection every 3 days, of either PBS (control), 5-FU (20 mg/kg), Lithium Chloride (200 mg/kg) or combinations of 5-FU (20 mg/kg) and Lithium Chloride (200 mg/kg) for 4-6 weeks. All animals were euthanized, lungs removed and weighed and examined for signs of metastatic disease. The average lung weights are presented as mean+/−SEM.
Figure 18:
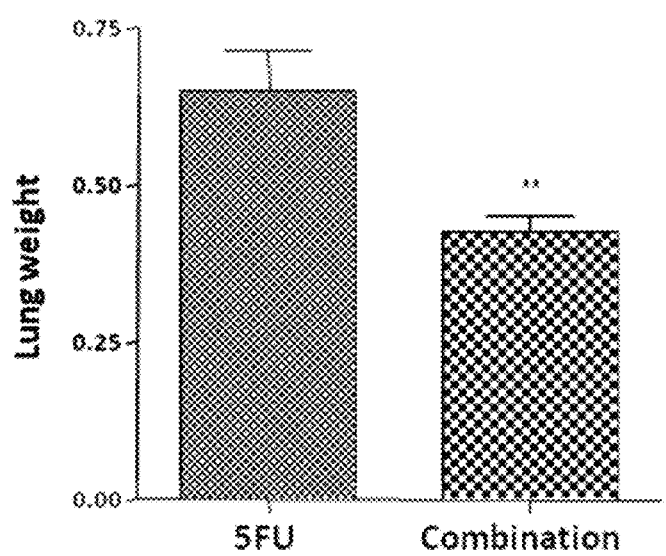
Figure 19A:
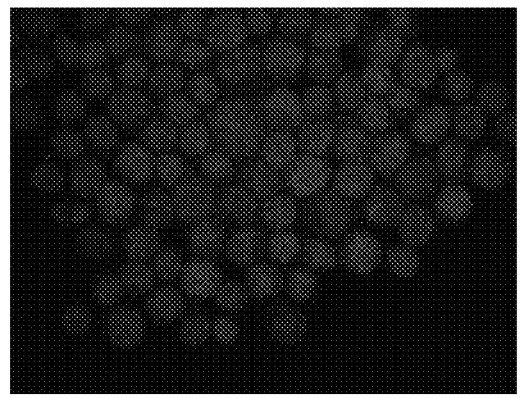
FIG. 19 Antitumour effect of combination therapy of 5-FU and Lithium Chloride on Lewis lung carcinoma derived tumours in a MF1 nu/nu murine model. Enhanced levels of autophagy/type II cell death are detected in LLC-Luc cells, treated with 5-FU in vitro (B) & (C). FITC conjugated LC3 (a known marker of autophagy), forms a green punctate staining pattern in the cytoplasm when it accumulates in forming autophagosomes. Control LLC-Luc cells (A) exhibit basal levels of autophagy, with low levels of autophagosome formation. Following treatment the number of cells and the extent of autophagy is greatly enhanced, at 24(B) and 48(C) hours.
Figure 19B:
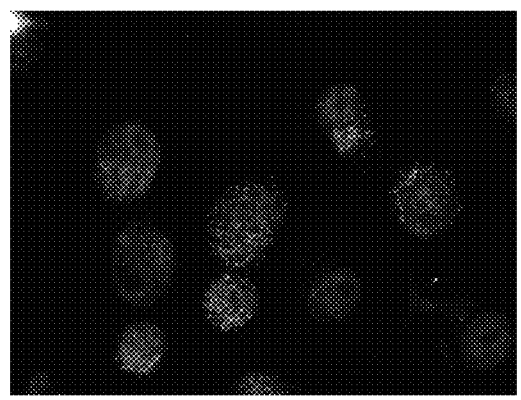
Figure 19C:
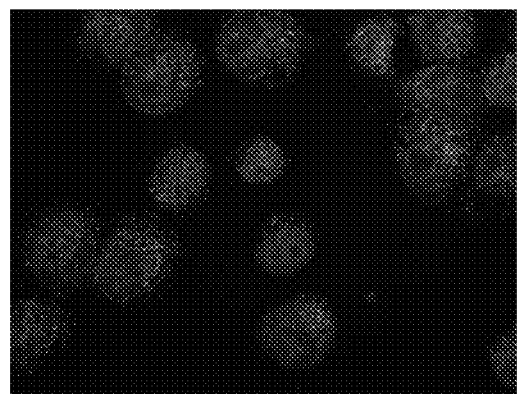

Combination treatments with 5-FU and Lithium chloride significantly reduced LLC-Luc derived tumours in a murine model, when compared to treatment (via localised and systemic delivery) with either 5-FU or Lithium alone, while also reducing the spread/metastatic burden from LLC (WT) derived tumours (FIGS. 17-19).

Figure 20:
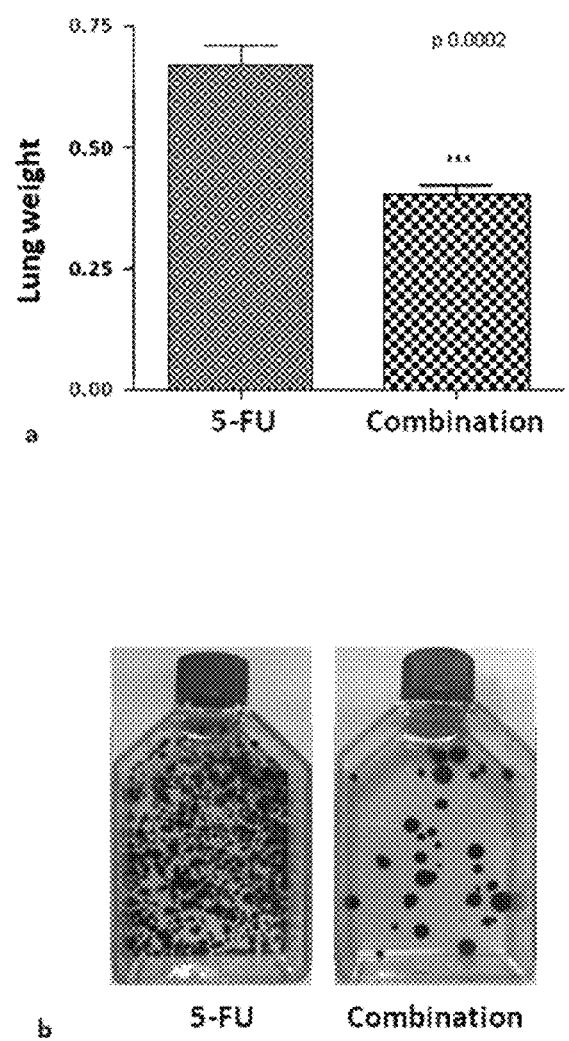
FIG. 20 In vivo implementation in pre-clinical Breast Carcinoma model: Enhanced Autophagy Therapy reduces Metastatic Burden To further assess the antitumour effect of systemically delivered treatment on metastatic disease, a spontaneously metastasizing mammary adenocarcinoma model (4T1) in Balb/c mice is utilized. a 4T1 breast carcinoma cells ($1\times10^5$ cells) (spontaneously metastasize to the lung) were injected into the right flank of Balb/c adult female mice after anaesthesia. Primary tumours were measured on alternative days following injection of tumour cells using a Vernier Calipers. Tumour diameter was measured and when mean tumour diameters were 8.0 mm+/−0.2 mm (~14 days post injection of tumour cells), primary tumours were excised and animals were randomized into 4 groups (n=10 per group). The treated and control groups received intraperitoneal injection every 3 days of either PBS (control), 5-FU (20 mg/kg), Lithium Chloride (200 mg/kg) or combinations of 5-FU (20 mg/kg) and Lithium Chloride (200 mg/kg) for 4-6 weeks. All animals were euthanized, lungs removed and weighed and examined for signs of metastatic disease. The average lung weights are presented as mean+/−SEM. b Additionally, following weighing, lungs from each group were dissociated and cells were cultured in a conditioned medium, containing 6-thio guanine (only 4T1 cells will grow in the presence of 6TG). 14 days after incubation, cells were washed, fixed and stained with Rapi-Diff II solution. Metastatic 4T1 cells now appear as blue colonies and can be counted to quantify the spread of a 4T1 metastatic disease in all lungs.

To further assess the antitumour effect of systemically delivered treatment on metastatic disease, a spontaneously metastasizing mammary adenocarcinoma model (4T1) in Balb/c mice was utilized. Combination treatments with 5-FU and Lithium chloride significantly reduced the spread or burden of metastatic disease in this spontaneously metastasizing breast carcinoma model, when compared to treatment with either 5-FU or Lithium alone, confirmed by both lung weights and the quantifiable 6-thio guanine assay (p=0.0002; FIG. 20).

Figure 22:
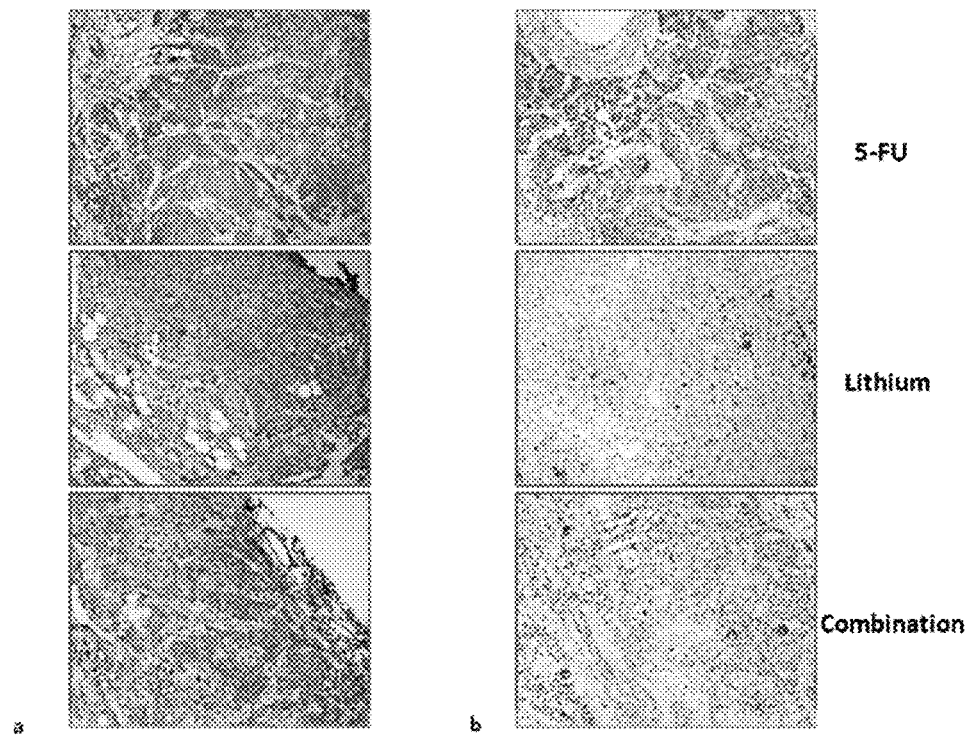
FIG. 22 In vivo implementation in pre-clinical Xenograft (Oesophageal carcinoma) model: Enhanced Autophagy Therapy enhances bio-markers of autophagy, in the absence of apoptosis. Tumours (Oesophageal KYSE450 derived tumours, developed in MF1 nu/nu mice) from treated animals were surgically removed, dissected, and immediately fixed with 10% neutral buffered formalin for 24 hour, processed by routine histology steps to be embedded in paraffin blocks. Five-micrometer-thick serial sections are cut with a microtome. For general histology, one section is stained by the hematoxylin and eosin (H&E) stain, and the remaining sections are for immunohistochemistry. Sections were stained for a LC3 (bio-marker of autophagy) and b active caspase3 (bio-marker of apoptosis). Methods include standard steps such as: De-paraffinising and rehydration of sections, Antigen retrieval, blocking of endogenous peroxidases, antibody staining and DAB detection methods. Tumours treated with combination therapy (20 mg/kg 5-FU & 200 mg/kg Lithium Chloride) display enhanced LC3 staining (as a result of augmented autophagy) in the absence of any detectable apoptosis.

Oesophageal KYSE450 derived tumours developed in MF1 nu/nu mice from treated animals were surgically removed, dissected, and processed by routine histology for immunohistochemistry analysis. Sections were stained for LC3 (bio-marker of autophagy) and active caspase3 (bio-marker of apoptosis). Tumours treated with combination therapy (20 mg/kg 5-FU & 200 mg/kg Lithium Chloride) display enhanced LC3 staining (as a result of augmented autophagy) in the absence of any detectable apoptosis (FIG. 22). As such, these findings demonstrate that enhanced autophagy therapy enhances bio-markers of autophagy, in the absence of apoptosis.

Figure 21:
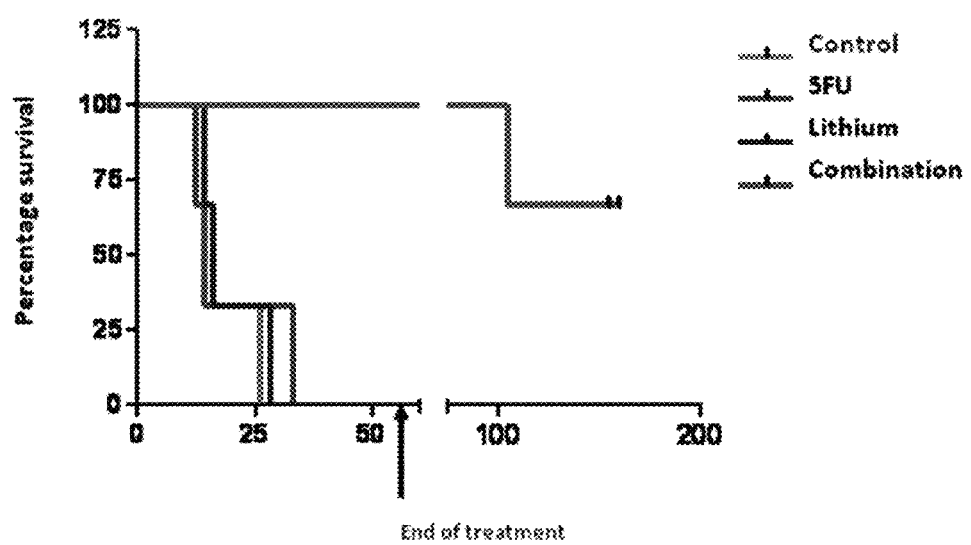
FIG. 21 In vivo implementation in pre-clinical Colorectal carcinoma model: Enhanced Autophagy Therapy enhances survival. For routine tumour induction, $1\times10^6$ CT26 (Colorectal carcinoma cells) suspended in 200 µl of serum free DMEM were injected subcutaneously into the right flank of adult female Balb/c mice, after anaesthesia. Mice were randomly divided into experimental groups. Mice were treated at a tumour volume of approximately 60 mm$^3$ in volume (5-7 mm major diameter). All treatments were delivered in 50 µl volumes, administered directly into the tumour, thrice weekly with PBS (Control), Lithium Chloride (200 mg/kg), 5-FU (20 mg/kg) and a combination of both Lithium and 5-FU (200 mg/kg, 20 mg/kg). Following drug treatment, tumours were monitored by alternate day measurements in two dimensions, using Verniers Calipers. Tumor volumes were calculated according to the formula $V=ab^2/6$, where 'a' is the longest diameter of the tumor and 'b' is the longest diameter perpendicular to diameter 'a'. Animals were culled when tumour volumes exceeded ~500 mm$^3$ (no greater than 15 mm in diameter). There were no control or lithium treated animals alive beyond day 28, and the final 5-FU treated animal was euthanized on day 33. At this point, all tumours on the combination treated animals were reduced to scabs. Treatment of these animals was maintained until day 58, following which all treatments ceased. 5 months after cessation of treatment these animals remain tumour free.

To investigate autophagy therapy in an in vivo pre-clinical colorectal carcinoma model, CT26 cells (Colorectal carcinoma cells) were injected subcutaneously into the right flank of adult female Balb/c mice, after anaesthesia. All treatments were delivered directly into the tumour, thrice weekly. Following drug treatment, tumours were monitored by alternate day measurements in two dimensions. There were no control or lithium treated animals alive beyond day 28, and the final 5-FU treated animal was euthanized on day 33. At this point, all tumours on the combination treated animals were reduced to scabs. Treatment of these animals was maintained until day 58, following which all treatments ceased. 5 months after cessation of treatment these animals remain tumour free (FIG. 21).

Figure 23:
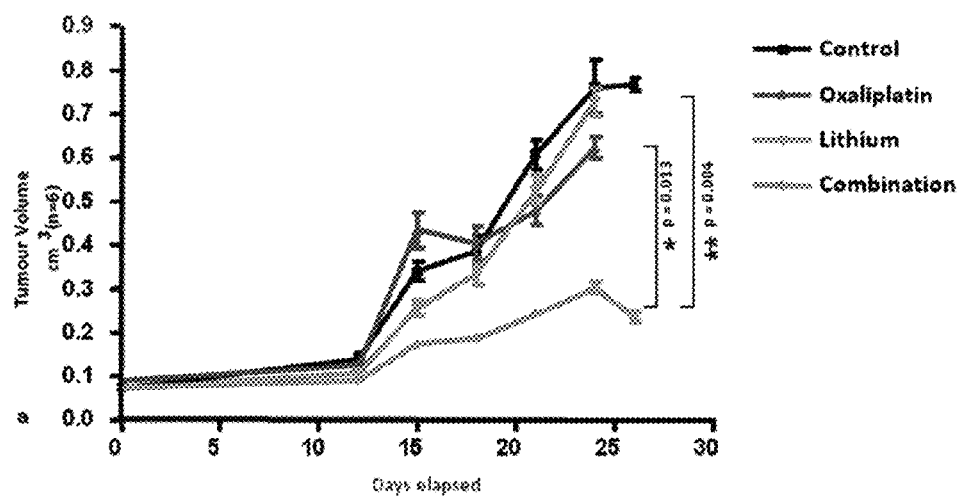
FIG. 23 In vivo implementation in pre-clinical Colorectal carcinoma model: Systemic delivery of Combination Therapy (Oxaliplatin & Lithium) reduces tumour growth and enhances survival. For routine tumour induction, $1\times10^6$ CT26 (Colorectal carcinoma cells) suspended in 200 µl of serum free DMEM were injected subcutaneously into the right flank of adult female Balb/c mice, after anaesthesia. Mice were randomly divided into experimental groups (n=6). Mice were treated at a tumour volume of approximately 60 mm$^3$ in volume (5-7 mm major diameter). All treatments were delivered in 55 µl volumes, administered via intraperitoneal injection, thrice weekly with PBS (Control), Lithium Chloride (200 mg/kg), Oxaliplatin (10 mg/kg) and a combination of both Lithium and Oxaliplatin (200 mg/kg, 10 mg/kg). Following drug treatment, tumours were monitored by alternate day measurements in two dimensions, using Verniers Calipers. Tumor volumes were calculated according to the formula $V=ab^2/6$, where 'a' is the longest diameter of the tumor and 'b' is the longest diameter perpendicular to diameter 'a'. Animals were culled when tumour volumes exceeded ~500 mm$^3$ (no greater than 15 mm in diameter).
Figure 23:
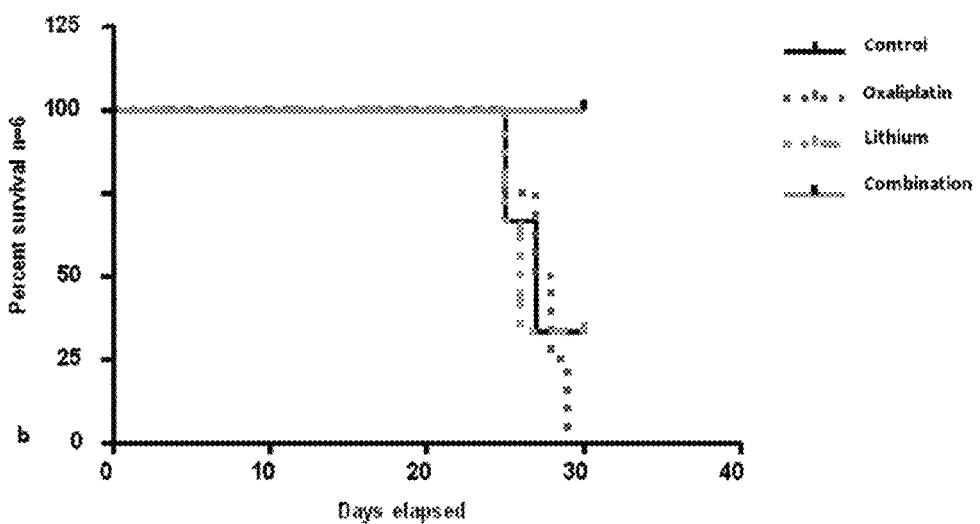

In an identical model system, Oxaliplatin (10 mg/kg) was used in place of 5-FU and a combination of both Lithium and Oxaliplatin (200 mg/kg, 10 mg/kg). The combination treatment had a significant effect on tumour volume, following systemic delivery when compared to both single agent treatments Oxaliplatin and Lithium (*p=0.013 and *p=0.004 respectively). This combination treatment also enhanced survival when compared to either agent alone (FIG. 23).

In vivo implementation in pre-clinical Colorectal carcinoma model: Enhanced Autophagy Therapy enhances survival. For routine tumour induction, $1 \times 10^6$ CT26 (Colorectal carcinoma cells) suspended in 200 µl of serum free DMEM are injected subcutaneously into the right flank of adult female Balb/c mice, after anaesthesia. Mice are randomly divided into experimental groups. Mice are treated at a tumour volume of approximately 60 $mm^3$ in volume (5-7 mm major diameter). All treatments are delivered in 501.11 volumes, administered directly into the tumour, thrice weekly with PBS (Control), Rapamycin (0.6-2 mg/kg), 5-FU (20 mg/kg) and a combination of both Rapamycin and 5-FU (0.6-2 mg/kg, 20 mg/kg). Following drug treatment, tumours are monitored by alternate day measurements in two dimensions, using Verniers Calipers. Tumor volumes are calculated according to the formula $V=ab^2/6$, where 'a' is the longest diameter of the tumor and 'b' is the longest diameter perpendicular to diameter 'a'. Animals are culled when tumour volumes exceed ~500 mm$^3$ (no greater than 15 mm in diameter). There are no control or rapamycin-treated animals alive beyond day 28, and the final 5-FU treated animal are euthanized on day 33. At this point, all tumours on the combination treated animals are reduced to scabs. Treatment of these animals is maintained until day 58, following which all treatments cease.

The invention is not limited to the embodiments heretofore described which may be varied in construction and detail without departing from the spirit of the invention.

The references cited below and throughout the specification are incorporated herein by reference.

REFERENCES

AMARAVADI, R. K., YU, D., LUM, J. J., BUT, T., CHRISTOPHOROU, M. A., EVAN, G. I., THOMAS-TIKHONENKO, A. & THOMPSON, C. B. (2007) Autophagy inhibition enhances therapy-induced apoptosis in a Myc-induced model of lymphoma. *J Clin Invest*, 117, 326-36.

BERRY, D. L. & BAEHRECKE, E. H. (2007) Growth arrest and autophagy are required for salivary gland cell degradation in *Drosophila*. *Cell*, 131, 1137-48.

BIEDERBICK, A., KERN, H. F. & ELSASSER, H. P. (1995) Monodansylcadaverine (MDC) is a specific in vivo marker for autophagic vacuoles. *Eur J Cell Biol*, 66, 3-14.

CLARKE, P. G. (1990) Developmental cell death: morphological diversity and multiple mechanisms. *Anat Embryol (Berl)*, 181, 195-213.

DEBNATH, J., BAEHRECKE, E. H. & KROEMER, G. (2005) Does autophagy contribute to cell death? *Autophagy*, 1, 66-74.

DEGENHARDT, K., MATHEW, R., BEAUDOIN, B., BRAY, K., ANDERSON, D., CHEN, G., MUKHERJEE, C., SHI, Y., GELINAS, C., FAN, Y., NELSON, D. A., JIN, S. & WHITE, E. (2006) Autophagy promotes tumor cell survival and restricts necrosis, inflammation, and tumorigenesis. *Cancer Cell*, 10, 51-64.

DEGTEREV, A. & YUAN, J. (2008) Expansion and evolution of cell death programmes. *Nat Rev Mol Cell Biol*, 9, 378-90.

JIN, S. & WHITE, E. (2008) Tumor suppression by autophagy through the management of metabolic stress. *Autophagy*, 4, 563-6.

KANZAWA, T., GERMANO, I. M., KOMATA, T., ITO, H., KONDO, Y. & KONDO, S. (2004) Role of autophagy in temozolomide-induced cytotoxicity for malignant glioma cells. *Cell Death Differ*, 11, 448-57.

KANZAWA, T., KONDO, Y., ITO, H., KONDO, S. & GERMANO, I. (2003) Induction of autophagic cell death in malignant glioma cells by arsenic trioxide. *Cancer Res*, 63, 2103-8.

LAM, D., KOSTA, A., LUCIANI, M. F. & GOLSTEIN, P. (2008) The inositol 1,4,5-trisphosphate receptor is required to signal autophagic cell death. *Mol Biol Cell*, 19, 691-700.

LEVINE, B., SINHA, S. & KROEMER, G. (2008) Bcl-2 family members: dual regulators of apoptosis and autophagy. *Autophagy*, 4, 600-6.

LIANG, X. H., JACKSON, S., SEAMAN, M., BROWN, K., KEMPKES, B., HIBSHOOSH, H. & LEVINE, B. (1999) Induction of autophagy and inhibition of tumorigenesis by beclin 1. *Nature*, 402, 672-6.

MIZUSHIMA, N. (2007) Autophagy: process and function. *Genes Dev*, 21, 2861-73.

MIZUSHIMA, N., LEVINE, B., CUERVO, A. M. & KLIONSKY, D. J. (2008) Autophagy fights disease through cellular self-digestion. *Nature*, 451, 1069-75.

MUNAFO, D. B. & COLOMBO, M. I. (2001) A novel assay to study autophagy: regulation of autophagosome vacuole size by amino acid deprivation. *J Cell Sci*, 114, 3619-29.

NIEMANN, A., TAKATSUKI, A. & ELSASSER, H. P. (2000) The lysosomotropic agent monodansylcadaverine also acts as a solvent polarity probe. *J Histochem Cytochem*, 48, 251-8.

O'SULLIVAN G, C., SHEEHAN, D., CLARKE, A., STUART, R., KELLY, J., KIELY, M. D., WALSH, T., COLLINS, J. K. & SHANAHAN, F. (1999) Micrometastases in esophagogastric cancer: high detection rate in resected rib segments. *Gastroenterology*, 116, 543-8.

OPIPARI, A. W., JR., TAN, L., BOITANO, A. E., SORENSON, D. R., AURORA, A. & LIU, J. R. (2004) Resveratrol-induced autophagocytosis in ovarian cancer cells. *Cancer Res*, 64, 696-703.

PATTINGRE, S., ESPERT, L., BIARD-PIECHACZYK, M. & CODOGNO, P. (2008) Regulation of macroautophagy by mTOR and Beclin 1 complexes. *Biochimie*, 90, 313-23.

PATTINGRE, S., TASSA, A., QU, X., GARUTI, R., LIANG, X. H., MIZUSHIMA, N., PACKER, M., SCHNEIDER, M. D. & LEVINE, B. (2005) Bcl-2 antiapoptotic proteins inhibit Beclin 1-dependent autophagy. *Cell*, 122, 927-39.

QU, X., YU, J., BHAGAT, G., FURUYA, N., HIBSHOOSH, H., TROXEL, A., ROSEN, J., ESKELINEN, E. L., MIZUSHIMA, N., OHSUMI, Y., CATTORETTI, G. & LEVINE, B. (2003) Promotion of tumorigenesis by heterozygous disruption of the beclin 1 autophagy gene. *J Clin Invest*, 112, 1809-20.

RAGUZ, S. & YAGUE, E. (2008) Resistance to chemotherapy: new treatments and novel insights into an old problem. *Br J Cancer*, 99, 387-91.

RICCI, M. S. & ZONG, W. X. (2006) Chemotherapeutic approaches for targeting cell death pathways. *Oncologist*, 11, 342-57.

RYAN, P., MCCARTHY, S., KELLY, J., COLLINS, J. K., DUNNE, C., GROGAN, L., BREATHNACH, O., SHANAHAN, F., CAREY, P. D., WALSH, T. N. & O'SULLIVAN, G. C. (2004) Prevalence of bone marrow micrometastases in esophagogastric cancer patients with and without neoadjuvant chemoradiotherapy. *J Surg Res*, 117, 121-6.

SANT, M., AARELEID, T., BERRINO, F., BIELSKA LASOTA, M., CARLI, P. M., FAIVRE, J., GROSCLAUDE, P., HEDELIN, G., MATSUDA, T., MOLLER, H., MOLLER, T., VERDECCHIA, A., CAPOCACCIA, R., GATTA, G., MICHELI, A., SANTAQUILANI, M., ROAZZI, P. & LISI, D. (2003) EUROCARE-3: survival of cancer patients diagnosed 1990-94—results and commentary. *Ann Oncol*, 14 Suppl 5, v61-118.

SARKAR, S. & RUBINSZTEIN, D. C. (2006) Inositol and IP3 levels regulate autophagy: biology and therapeutic speculations. *Autophagy*, 2, 132-4.

SCARLATTI, F., GRANATA, R., MEIJER, A. J. & CODOGNO, P. (2009) Does autophagy have a license to kill mammalian cells? *Cell Death Differ*, 16, 12-20.

SCARLATTI, F., MAFFEI, R., BEAU, I., CODOGNO, P. & GHIDONI, R. (2008) Role of non-canonical Beclin 1-independent autophagy in cell death induced by resveratrol in human breast cancer cells. *Cell Death Differ*, 15, 1318-29.

TAKEUCHI, H., KONDO, Y., FUJIWARA, K., KANZAWA, T., AOKI, H., MILLS, G. B. & KONDO, S. (2005) Synergistic augmentation of rapamycin-induced autophagy in malignant glioma cells by phosphatidylinositol 3-kinase/protein kinase B inhibitors. *Cancer Res*, 65, 3336-46.

YORIMITSU, T. & KLIONSKY, D. J. (2005) Autophagy: molecular machinery for self-eating. *Cell Death Differ*, 12 Suppl 2, 1542-52.

YU, L., WAN, F., DUTTA, S., WELSH, S., LIU, Z., FREUNDT, E., BAEHRECKE, E. H. & LENARDO, M. (2006) Autophagic programmed cell death by selective catalase degradation. *Proc Natl Acad Sci USA*, 103, 4952-7.

ZHANG, L., MING, L. & YU, J. (2007) BH3 mimetics to improve cancer therapy; mechanisms and examples. *Drug Resist Updat*, 10, 207-17.

The invention claimed is:

1. A method for the treatment of a chemo-resistant cancer in an individual comprising a step of administering to the individual a therapeutically effective amount of at least one chemotherapeutic agent, wherein the chemotherapeutic agent is a DNA-binding platinum complex, and at least one autophagy inducer, wherein the chemo-resistant cancer exhibits autophagy and has a non-apoptotic phenotype, wherein the autophagy inducer is administered in an amount that induces the death of cancer cells by induction of autophagy.

2. The method of claim 1 in which the DNA-binding platinum complex is selected from the group consisting of carboplatin, cisplatin, or oxaliplatin.

3. The method of claim 1 in which the cancer is an epithelial cancer.

4. The method of claim 3 in which the epithelial cancer is selected from the group consisting of a lung, breast, colorectal, and an esophagogastric cancer, or their metastases.

5. The method of claim 1 in which the at least one autophagy inducer is a lithium salt.

* * * * *